US008802895B2

(12) United States Patent
Su et al.

(10) Patent No.: US 8,802,895 B2
(45) Date of Patent: Aug. 12, 2014

(54) AMIDE DERIVATIVES OF BENZENE-SULFONANILIDE, PHARMACEUTICAL COMPOSITION THEREOF AND METHOD FOR CANCER TREATMENT USING THE SAME

(75) Inventors: Bin Su, Westlake, OH (US); Aimin Zhou, Solon, OH (US); Yan Xu, Solon, OH (US)

(73) Assignee: Cleveland State University, Cleveland, OH (US)

(*) Notice: Subject to any disclaimer, the term of this patent is extended or adjusted under 35 U.S.C. 154(b) by 537 days.

(21) Appl. No.: 12/906,315

(22) Filed: Oct. 18, 2010

(65) Prior Publication Data
US 2012/0095092 A1   Apr. 19, 2012

(51) Int. Cl.
C07C 303/00   (2006.01)
(52) U.S. Cl.
USPC ............................................. 564/98
(58) Field of Classification Search
USPC ............................................. 564/98
See application file for complete search history.

(56) References Cited

U.S. PATENT DOCUMENTS

| 6,469,040 B2 | 10/2002 | Seibert et al. |
| 7,741,520 B2 | 6/2010 | Brueggemeier et al. |
| 2006/0217389 A1 | 9/2006 | Sun et al. |

FOREIGN PATENT DOCUMENTS

WO   WO 2007/120379 A2   10/2007

OTHER PUBLICATIONS

Gueto, C. et al., European J Medicinal Chem (2009), 44(9), 3445-3451.*
Int'l Search Report, PCT/US 11/56619, Mailed Feb. 28, 2012, Completed Feb. 15, 2012, Lee W. Young, Authorized Officer.
Bin Su, Michael V. Darby and Robert W. Brueggemeier, "Synthesis and Biological Evaluation of Novel Sulfonanilide Compounds as Antiproliferative Agents for Breast Cancer," *Journal of Combinatorial Chemistry*, 2008, vol. 10, No. 3, pp. 475-483, American Chemical Society.
Bin Su and Shiuan Chen, "Lead optimization of COX-2 inhibitor nimesulide analogs to overcome aromatase inhibitor resistance in breast cancer cells," *Bioorganic & Medicinal Chemistry Letters* 19 (2009), pp. 6733-6735, Elsevier Ltd.
Bin Chen, Bin Su and Shiuan Chen, "A COX-2 inhibitor nimesulide analog selectively induces apoptosis in Her2 overexpressing breast cancer cells via cytochrome c dependent mechanisms," *Biochemical Pharmacology* 77 (2009), pp. 1787-1794, Elsevier Inc.

* cited by examiner

*Primary Examiner* — Porfirio Nazario Gonzalez
*Assistant Examiner* — Kofi Adzamli
(74) *Attorney, Agent, or Firm* — Fay Sharpe LLP

(57) ABSTRACT

The invention provides a compound of formula (I), a pharmaceutical composition thereof, a method of preparing a medicament for the treatment of a cancer, and a method of treating cancers. The invention exhibits merits against cancers such as significantly higher potency and effectiveness over a broader range of cancers. In formula (I), $R_a$ is a benzyl group with alkyl and/or alkoxy; $R_b$ is selected from H and alkyl groups; $R_f$ is an alkyl; and $R_3$ is selected from a substituted phenyl, a heterocyclic group, and

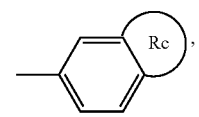

wherein Rc is selected from a fused ring, fused rings, and any bivalent cyclic group.

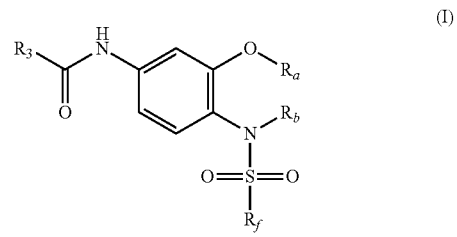

27 Claims, 11 Drawing Sheets

AMIDE DERIVATIVES OF BENZENE-SULFONANILIDE, PHARMACEUTICAL COMPOSITION THEREOF AND METHOD FOR CANCER TREATMENT USING THE SAME

BACKGROUND OF THE INVENTION

The invention relates to a new class of compounds, a pharmaceutical composition thereof, a method of preparing a medicament for the treatment of a cancer, and a method of treating cancers. It finds particular application in conjunction with the treatment of breast cancer, colon cancer, CNS cancer, leukemia, melanoma, non-small cell lung cancer, ovarian cancer, renal cancer, and prostate cancer, and will be described with particular reference thereto. However, it is to be appreciated that the present exemplary embodiment is also amenable to other like applications.

Epidemiological and animal model studies have suggested that nonsteroidal anti-inflammatory drugs (NSAIDs) may also act as chemopreventive agents. The premise that cyclooxygenase-2 (COX-2) inhibition is integral to this anti-carcinogenic effect is based on the assumption that COX-2 generated prostaglandins (PGEs) promote tumor growth in an autocrine and/or paracrine manner. The inhibition of COX-2 activity by traditional NSAIDs blocks these activities and thus may account for the anticarcinogenic activity of these drugs. However, an expanding body of evidence suggests that COX-2-independent mechanism may also be involved in the antitumor effect of COX-2 inhibitors.

Nimesulide (4-nitro-2-phenoxymethane-sulfoanilide) is a nonsteroidal anti-inflammatory drug with a preferential COX-2 inhibitory activity and has been available in some Asian and European countries since 1985. Furthermore, some studies have also demonstrated the anti-cancer activity of nimesulide during the past decade. For example, U.S. Pat. No. 7,741,520 issued to Brueggemeier et al. has disclosed that some sulfonanilide analogs can be used as selective aromatase modulators (SAMs) to suppress aromatase activity expression in breast cancer cells. Nimesulide can induce apoptosis in liver and lung cancer cells, and it also suppresses the development of 2-amino-1-methyl-6-phenylimidazo[4,5-b]pyridine (PhIP)-induced mammary gland carcinogenesis in rats. However, problems associated with nimesulide and its known derivatives include that, as general anti-cancer agents, they exhibit only low to moderate potency on a narrow range of cancers.

Advantageously, the present invention provides a new compound, a pharmaceutical composition containing the compound, a method of preparing a medicament for the treatment of a cancer using the compound, and a method of treating a cancer. The invention overcomes the aforementioned problems, and exhibits merits against cancers such as significantly higher potency, and effectiveness over a broader range of cancers, among others.

BRIEF DESCRIPTION OF THE INVENTION

One aspect of the invention provides a compound of formula (I):

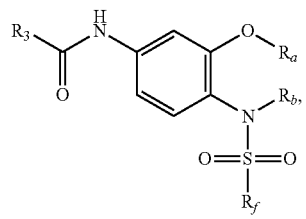

wherein $R_a$ is selected from dialkoxybenzyl, alkylalkoxybenzyl, dialkylbenzyl, trialkoxybenzyl, alkyldialkoxybenzyl, alkoxydialkylbenzyl, and trialkylbenzyl; $R_b$ is selected from H and alkyl groups, such as $C_1$-$C_6$ alkyl groups, e.g. methyl, ethyl, n-propyl, and isopropyl; $R_f$ is an alkyl such as methyl and ethyl; and $R_3$ is selected from monosubstituted phenyl, disubstituted phenyl, trisubstituted phenyl, heterocyclic group, and

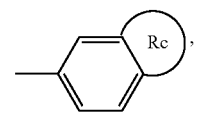

wherein Rc is selected from a fused ring, fused rings, and any bivalent cyclic group.

Another aspect of the invention provides a pharmaceutical composition comprising an effective amount of the compound of formula (I) or a pharmaceutically acceptable salt thereof, and a pharmaceutically acceptable carrier.

Still another aspect of the invention provides a method of preparing a medicament for the treatment of a cancer, comprising the step of including a compound of formula (I) or a pharmaceutically acceptable salt thereof into the medicament.

A further aspect of the invention provides a method of treating a cancer, comprising administering to a mammal a therapeutically effective amount of the compound of formula (I) or a pharmaceutically acceptable salt thereof.

DETAILED DESCRIPTION OF THE INVENTION

Figure 1:
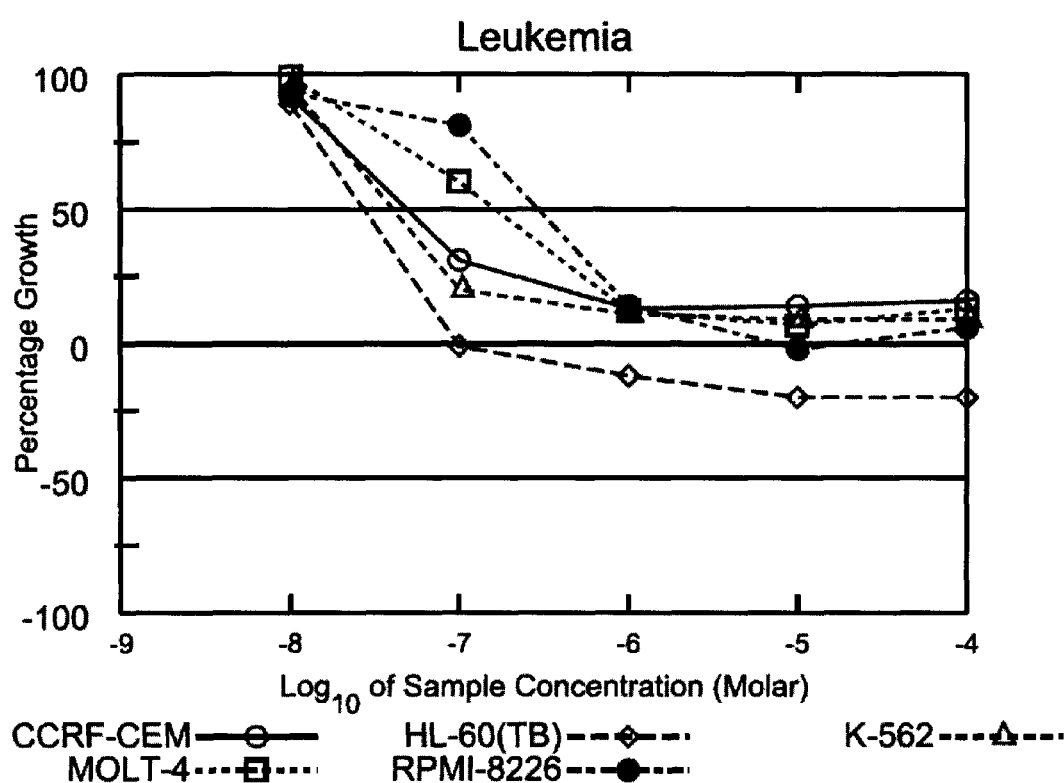
FIGS. 1-9 show the dose responsive curves of leukemia, non-small cell lung cancer, colon cancer, CNS cancer, melanoma, ovarian cancer, renal cancer, prostate cancer and breast cancer, respectively, to a compound of formula (I) in accord with different embodiments of the invention.
Figure 2:
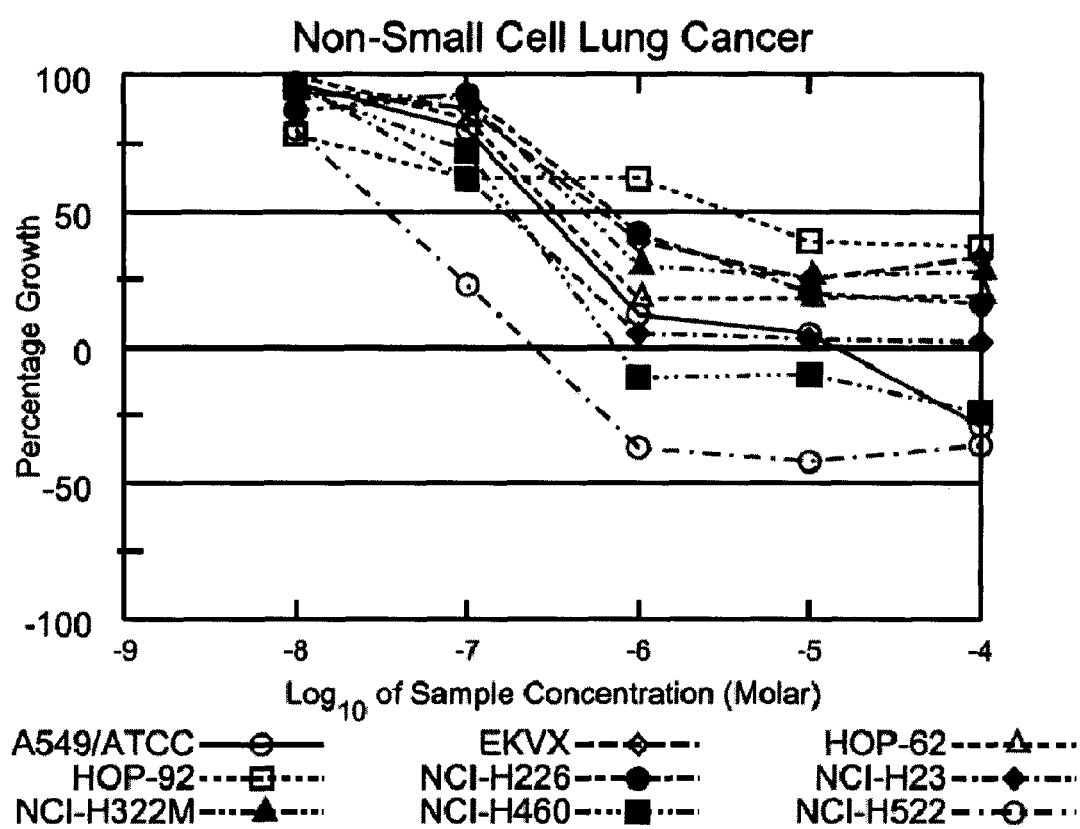
Figure 3:
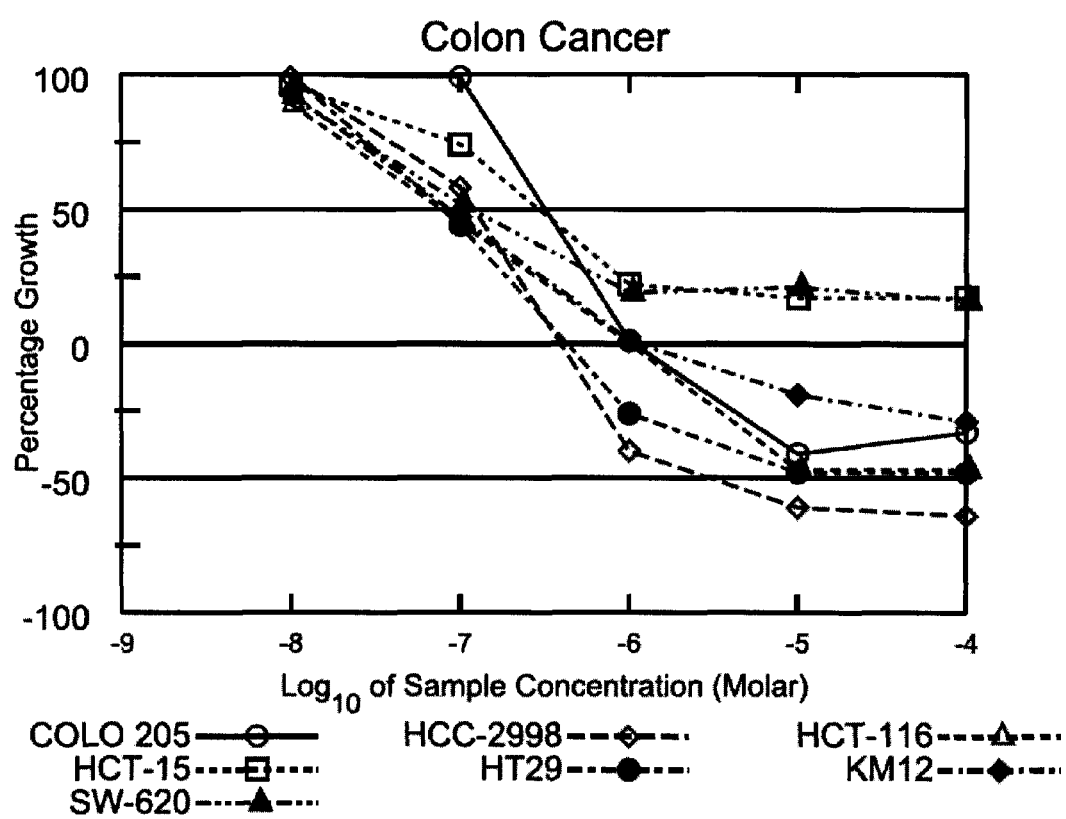
Figure 4:
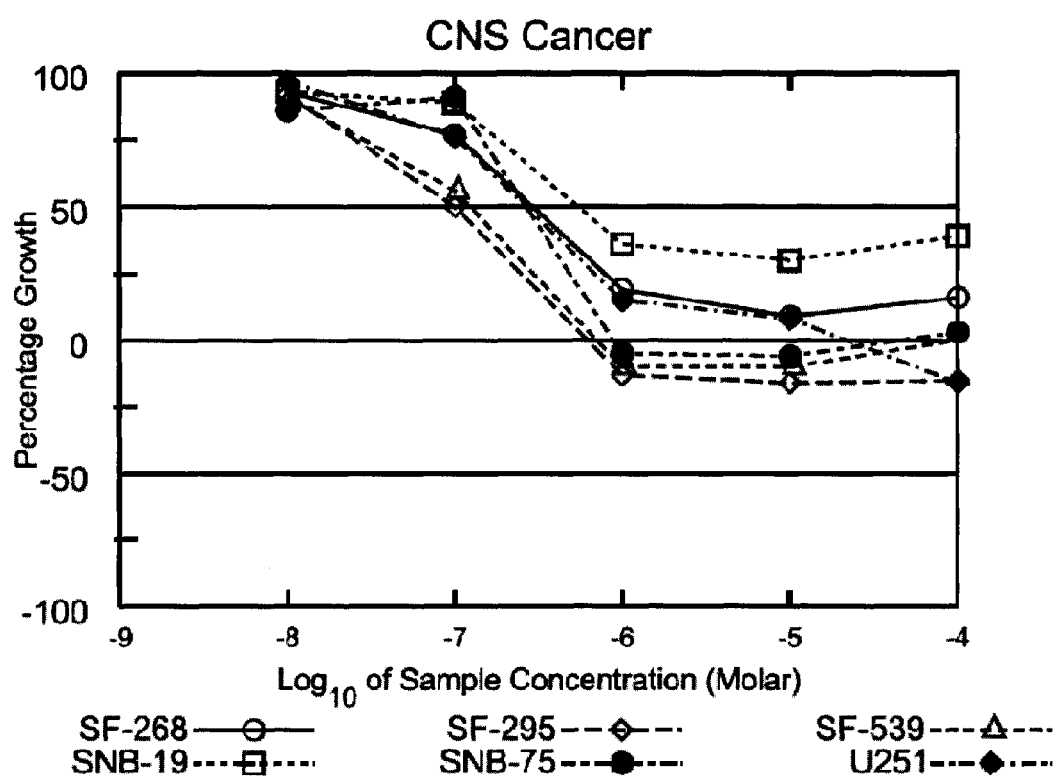
Figure 5:
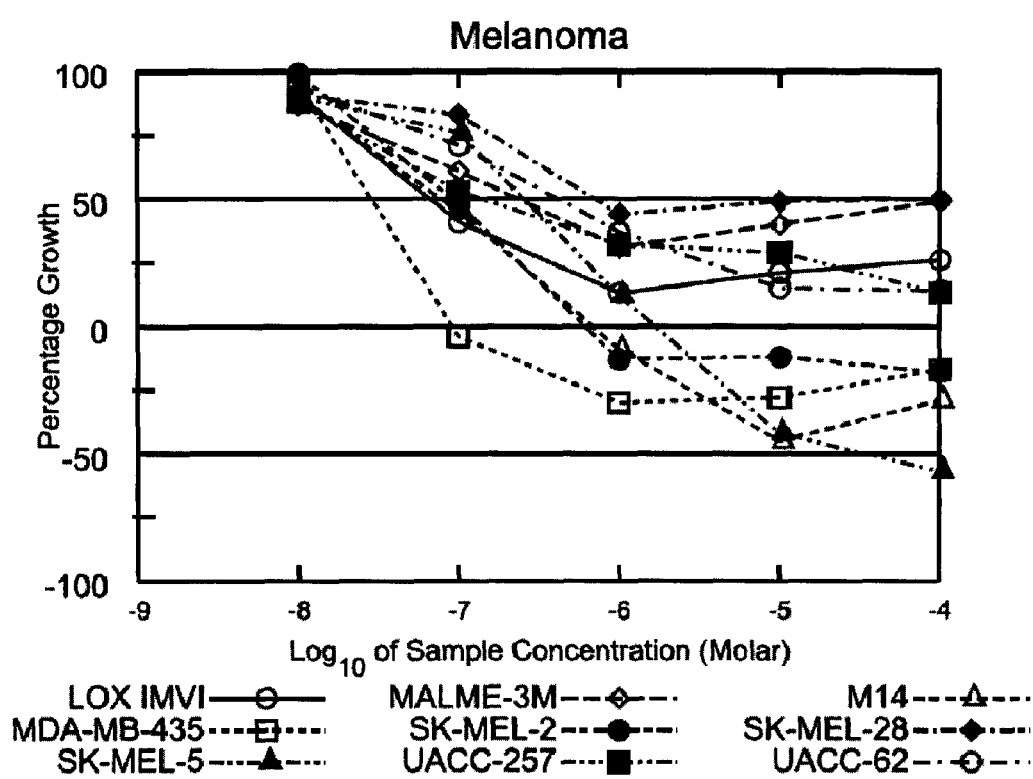
Figure 6:
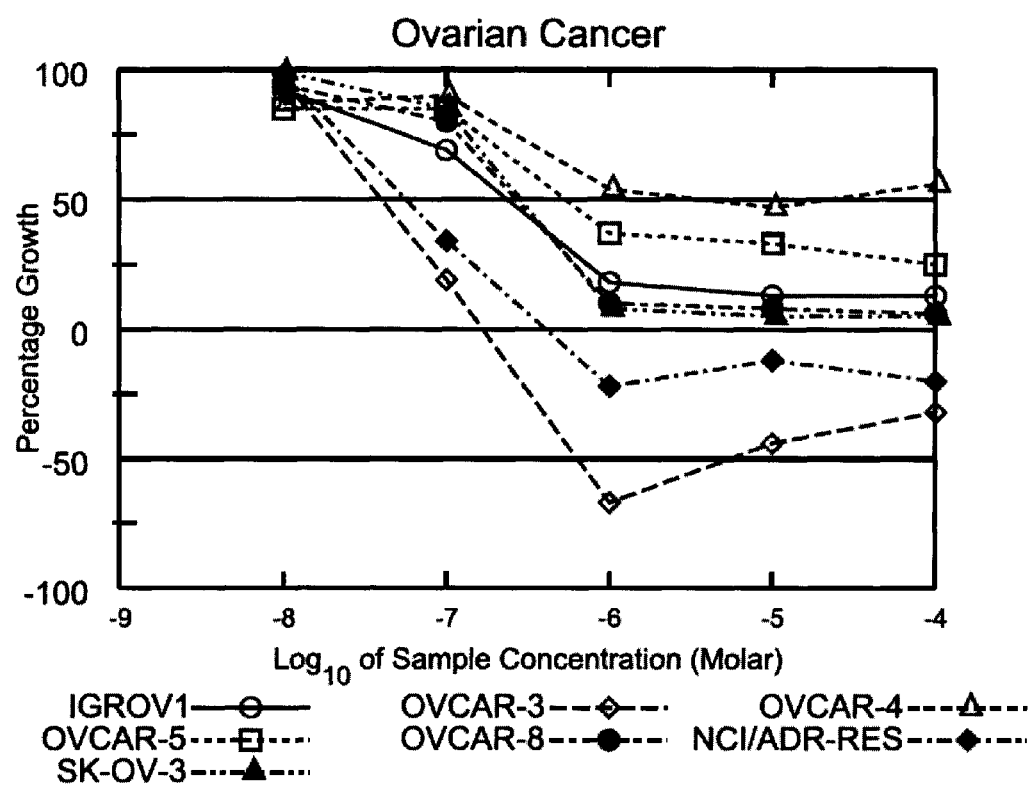
Figure 7:
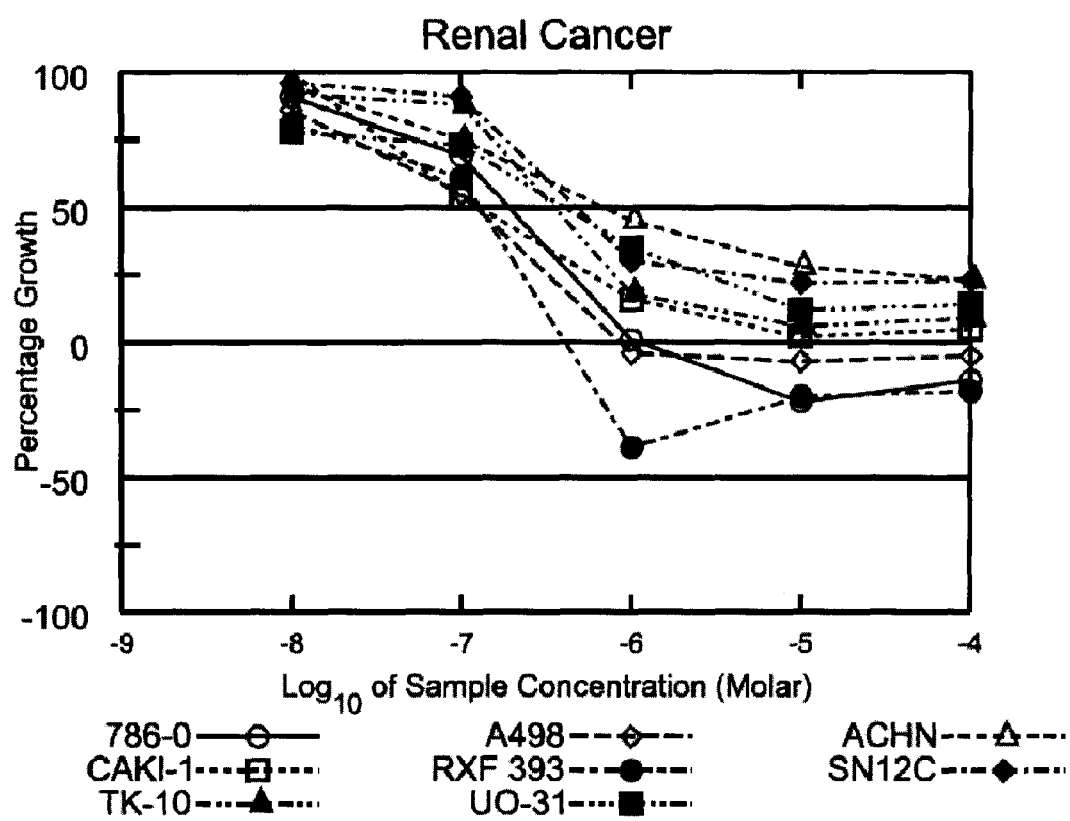
Figure 8:
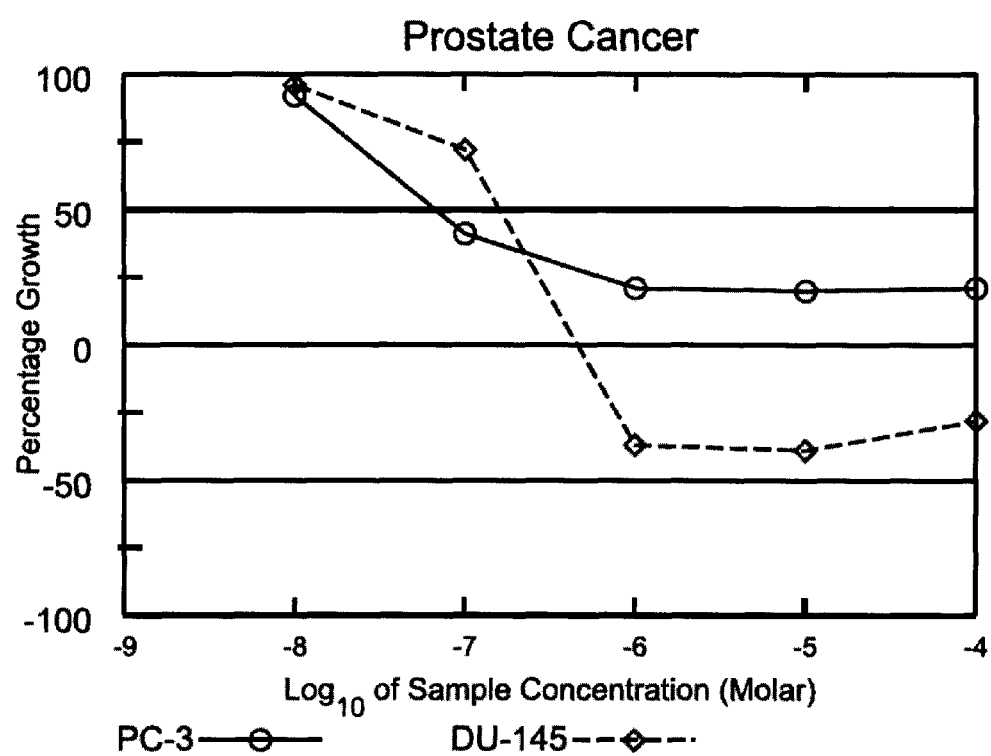
Figure 9:
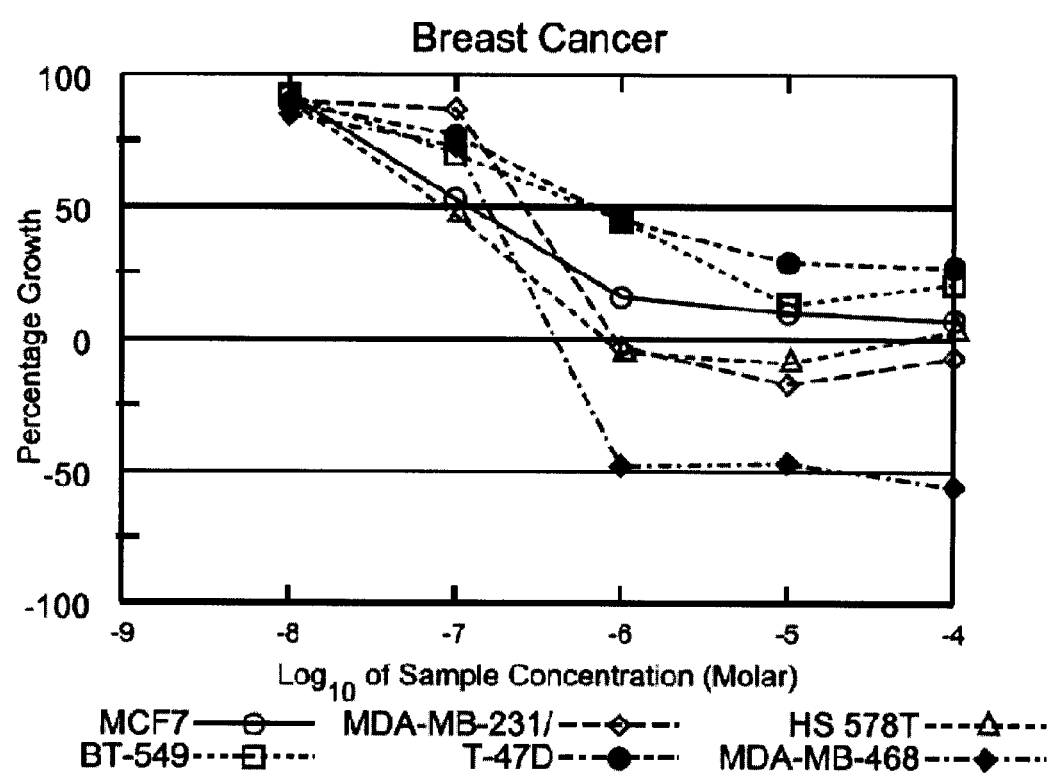

The invention relates to a new class of compounds and to pharmaceutical compositions including the compound for use in cancer treatment, as well as the method for using the same. It finds particular application in conjunction with the treatment of breast cancer, colon cancer, CNS cancer, leukemia, melanoma, non-small cell lung cancer, ovarian cancer, renal cancer, and prostate cancer.

The compound of interest corresponds to formula (I):

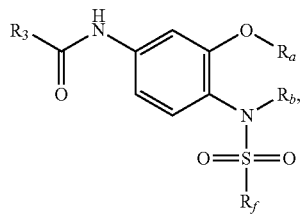

(I)

wherein $R_a$ is selected from dialkoxybenzyl, alkylalkoxybenzyl, dialkylbenzyl, trialkoxybenzyl, alkyldialkoxybenzyl, alkoxydialkylbenzyl, and trialkylbenzyl; $R_b$ is selected from H and alkyl groups, such as $C_1$-$C_6$ alkyl groups, e.g. methyl, ethyl, n-propyl, and isopropyl; $R_f$ is an alkyl such as methyl and ethyl; and $R_3$ is selected from monosubstituted phenyl, disubstituted phenyl, trisubstituted phenyl, heterocyclic group, and

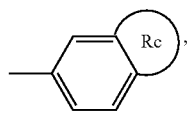

wherein Rc is selected from a fused ring, fused rings, and any bivalent cyclic group.

In various embodiments, $R_a$ in the compound of formula (I) may be selected from dialkoxybenzyl such as dimethoxybenzyl, diethoxybenzyl, and methoxyethoxybenzyl; alkylalkoxybenzyl such as methylmethoxybenzyl, methylethoxybenzyl, ethylmethoxybenzyl, and ethylethoxybenzyl; dialkylbenzyl such as dimethylbenzyl, diethylbenzyl, and methylethylbenzyl; trialkoxybenzyl such as trimethoxybenzyl, triethoxybenzyl, methoxydiethoxybenzyl, and dimethoxyethoxybenzyl; alkyldialkoxybenzyl such as methyldimethoxybenzyl, methylmethoxyethoxybenzyl, methyldiethoxybenzyl, ethyldimethoxybenzyl, ethyl methoxyethoxybenzyl, and ethyldiethoxybenzyl; alkoxydialkylbenzyl such as methoxydimethylbenzyl, methoxymethylethylbenzyl, methoxydiethylbenzyl, ethoxydimethylbenzyl, ethoxymethylethylbenzyl, and ethoxydiethylbenzyl; and trialkylbenzyl such as trimethylbenzyl, methyldiethylbenzyl, dimethylethylbenzyl, triethylbenzyl, methyldiethylbenzyl, and dimethylethylbenzyl. In an embodiment, $R_a$ in the compound of formula (I) is represented by:

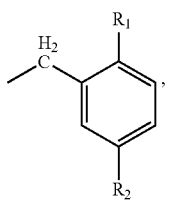

wherein $R_1$ and $R_2$ are independently of each other selected from alkyl such as methyl, ethyl, and propyl; and alkoxy such as methoxy, ethoxy, and propoxy.

In the first category of embodiments, $R_1$ and $R_2$ are independently of each other selected from alkoxy groups such as methoxy, ethoxy, and propoxy, and $R_3$ in the compound of formula (I) is selected from:

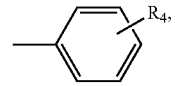

wherein $R_4$ is selected from halogens such as F, Cl, Br, and I; aryl groups, such as phenyl or substituted phenyl; and alkoxy groups, such as methoxy, ethoxy, and propoxy;

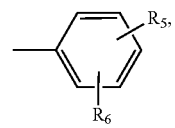

wherein $R_5$ and $R_6$ are independently of each other selected from alkoxy groups, such as methoxy, ethoxy, and propoxy; and

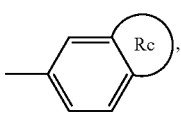

wherein Rc is selected from a fused ring, fused rings, and any bivalent carbon- or hetero-cyclic group. Examples of compounds in this group include, but are not limited to, those where $R_b$ is methyl, $R_f$ is methyl, $R_1$ is methoxy, and $R_2$ is methoxy.

In specifically exemplified embodiments of the invention, $R_b$ is methyl, $R_f$ is methyl, $R_1$ is methoxy, $R_2$ is methoxy, and $R_3$ is selected from:

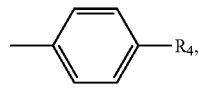

wherein $R_4$ is selected from Br, I, $OCH_3$, phenyl, and substituted phenyl;

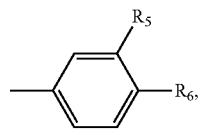

wherein $R_5$ and $R_6$ are both $OCH_3$;

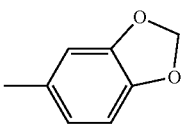

(3,4-(methylenedioxy)phenyl); and

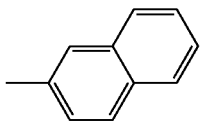

(napthyl such as 2-napthyl).

In a specific embodiment, the present invention provides a compound of formula (II):

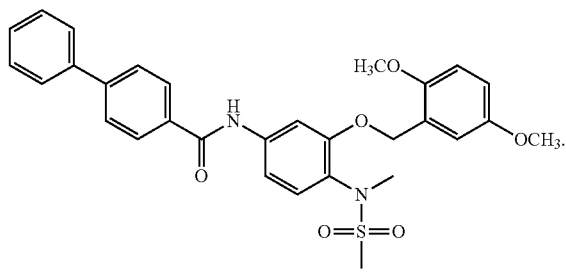

(II)

In the second category of embodiments, $R_1$ and $R_2$ are independently of each other selected from alkyl groups such as methyl, ethyl, and propyl. For example, $R_b$, $R_f$, $R_1$ and $R_2$ may all be methyl.

In an embodiment of this category, $R_b$, $R_f$, $R_1$ and $R_2$ are all methyl, and $R_3$ is selected from a phenyl group which is mono-, di-, or tri-phenyl substituted with halogen, alkoxy, alkylthio, and halo-substituted alkoxy; and

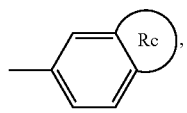

wherein Rc is selected from a fused ring, fused rings, and any bivalent carbon- or hetero-cyclic group.

In specifically exemplified embodiments of the invention, $R_b$, $R_f$, $R_1$ and $R_2$ are all methyl, and $R_3$ is selected from:

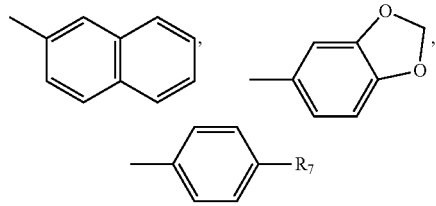

(wherein $R_7$ is Br, I, —OCH$_3$, —OCH$_2$CH$_3$, —SCH$_3$, and —OCF$_3$),

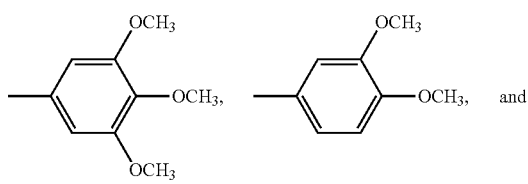

and

-continued

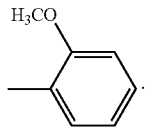

In the third category of embodiments, $R_3$ is heterocyclic group; and $R_1$ and $R_2$ are independently of each other selected from alkyl groups such as methyl, ethyl, and propyl. For example, $R_b$, $R_f$, $R_1$ and $R_2$ may all be methyl.

In specifically exemplified embodiments of the invention, $R_b$, $R_f$, $R_1$ and $R_2$ are all methyl, and $R_3$ is selected from:

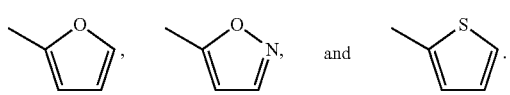

In exemplified embodiments, the invention provides specific compounds of formula (I), as shown in Tables 1-4.

TABLE 1

2,5-Dimethyl benzyl analogs

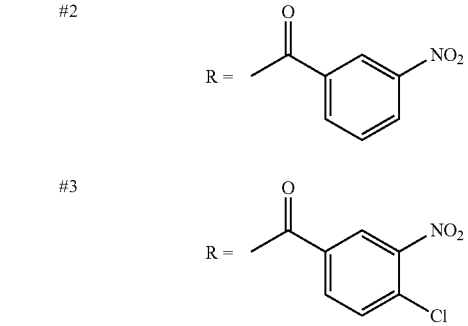

| Compound Code | |
|---|---|
| #1 | R = (4-nitrobenzoyl) |
| #2 | R = (3-nitrobenzoyl) |
| #3 | R = (3-nitro-4-chlorobenzoyl) |
| #4 | R = (3,4-dichlorobenzoyl) |

TABLE 1-continued
2,5-Dimethyl benzyl analogs
| Compound Code | |
|---|---|
| #5 | 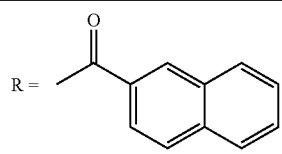 |
| #6 | 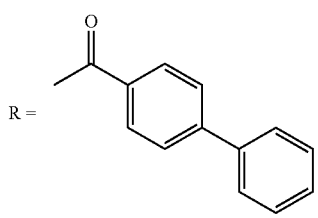 |
| #7 | 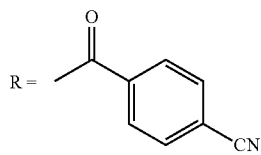 |
| #8 | 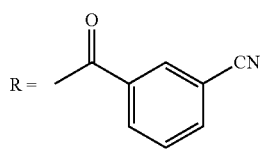 |
| #9 | 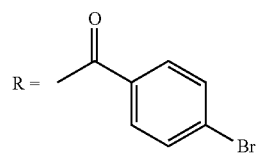 |
| #10 (NSC751382) | 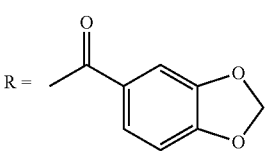 |
| #11 | 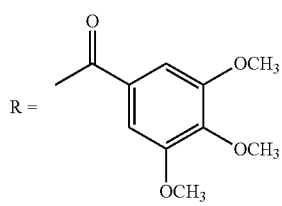 |
| #12 | 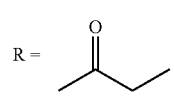 |
TABLE 1-continued
2,5-Dimethyl benzyl analogs
| Compound Code | |
|---|---|
| #13 | 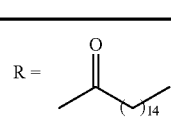 |
| #14 | 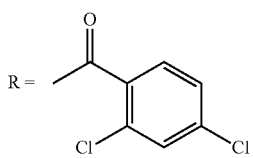 |
| #15 | 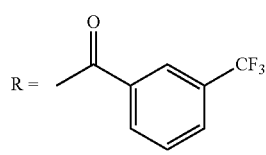 |
| #16 | 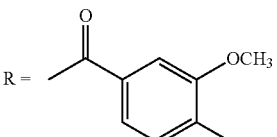 |
| #17 | 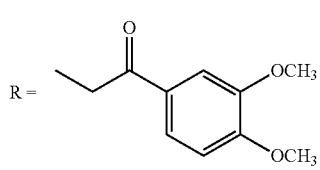 |
| #18 | 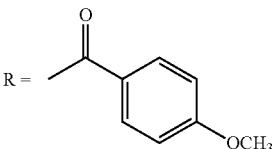 |
| #19 | 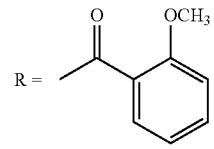 |
| #20 | 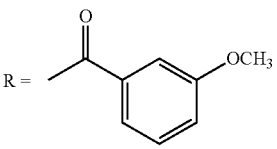 |

TABLE 1-continued
2,5-Dimethyl benzyl analogs
| Compound Code | |
|---|---|
| #21 | 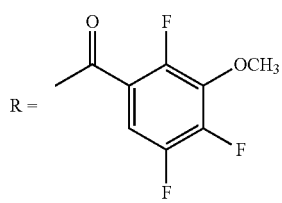 |
| #22 | 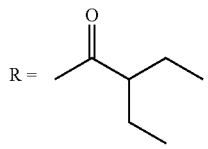 |
| #23 | 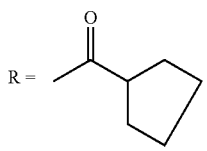 |
| #24 | 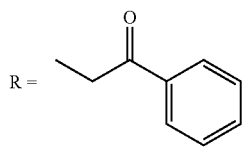 |
| #25 | 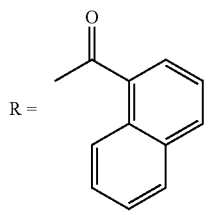 |
| #26 | 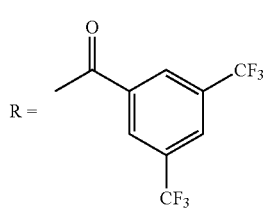 [SMILES: CC(=O)c1cc(C(F)(F)F)cc(C(F)(F)F)c1] |
| #27 | 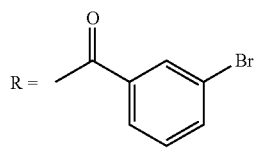 |
| #28 | 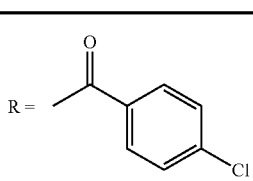 |
| #29 | 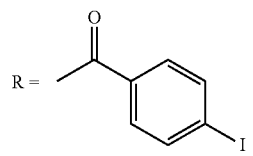 |
| #30 | 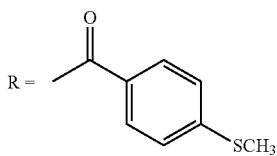 |
| #31 | 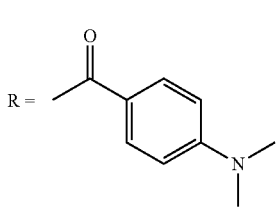 |
| #32 | 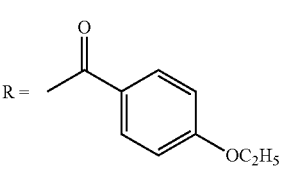 |
| #33 | 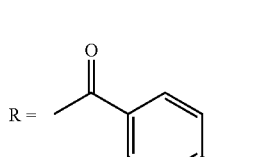 |
| #34 | 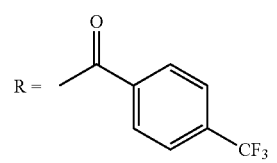 |

TABLE 1-continued
2,5-Dimethyl benzyl analogs
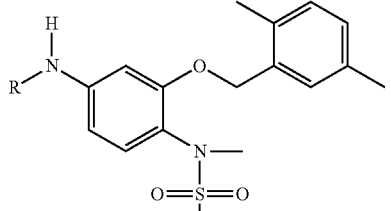
| Compound Code | |
|---|---|
| #35 | 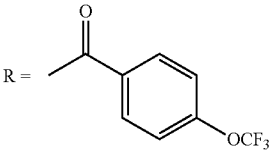 R = |
| #36 | 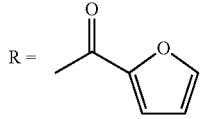 R = |
| #37 | 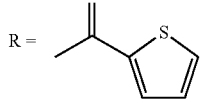 R = |
| #38 | 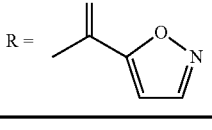 R = |
| #39 | 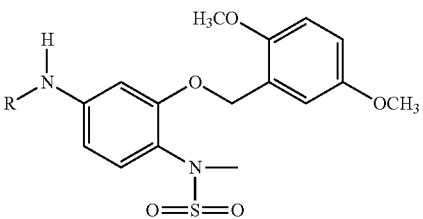 R = |
TABLE 2
2,5-Dimethoxyl benzyl analogs
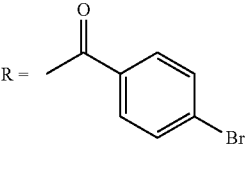
| Compound Code | |
|---|---|
| #40 | 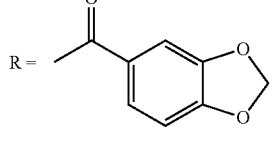 R = |
TABLE 2-continued
2,5-Dimethoxyl benzyl analogs
| Compound Code | |
|---|---|
| #41 | R = 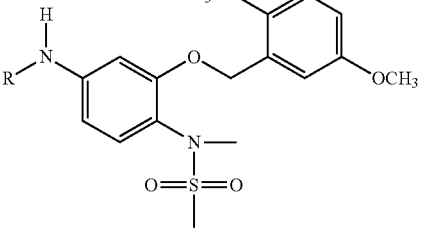 |
| #42 | R = |
| #43 | R = 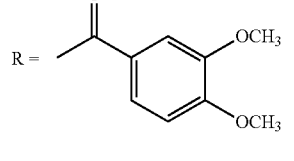 |
| #44 | R = |
| #45 | R = 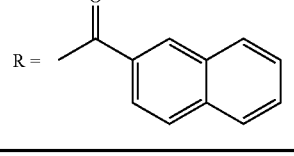 |

TABLE 3

2,5-Dichloro benzyl analogs

| Compound Code | R = |
|---|---|
| #46 | 4-bromobenzoyl |
| #47 | 4-methoxybenzoyl |
| #48 | 3,4-dimethoxybenzoyl |
| #49 | 4-iodobenzoyl |
| #50 | 2-naphthoyl |
| #51 | 1,3-benzodioxole-5-carbonyl |

TABLE 4

2-methyl-5-trifloromethyl benzyl analogs

| Compound Code | R = |
|---|---|
| #52 | 4-bromobenzoyl |
| #53 | 4-methoxybenzoyl |
| #54 | 3,4-dimethoxybenzoyl |
| #55 | 4-iodobenzoyl |
| #56 | 2-naphthoyl |
| #57 | 1,3-benzodioxole-5-carbonyl |

The pharmaceutical composition of the invention may comprise a pharmaceutical carrier and/or diluents. The composition may also comprise other agents in association with other chemotherapeutic or immunostimulating drugs or therapeutic agents. Examples of pharmaceutical carriers or diluents useful in the present invention include any physiological buffered medium, i.e., having a pH of about 7.0 to 7.4 comprising a suitable water soluble organic carrier. Suitable water soluble organic carriers include, but are not limited to, corn oil, dimethylsulfoxide, gelatin capsules, and other similar carriers.

The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of sulfonanilide compounds may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, galactaric, and galacturonic acids.

Suitable pharmaceutically acceptable base addition salts of sulfonanilide compounds include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used to form base addition salts of the sulfonanilide compounds. All of these salts may be prepared by conventional means from the corresponding sulfonanilide compounds by reacting, for example, the appropriate acid or base with the sulfonanilide compound.

The invention also provides a method of preparing a medicament for the treatment of a cancer, comprising a step of including a compound of formula (I) or a pharmaceutically acceptable salt thereof into the medicament. Cancers that may be treated may be selected from cancers that are vulnerable to the interference of the calcium signal transduction in the cancer cells.

In various embodiments of the method, the cancer is selected from breast cancer, colon cancer, CNS cancer, leukemia, melanoma, non-small cell lung cancer, ovarian cancer, renal cancer, and prostate cancer. For example, the compound of formula (I) may be selected from:

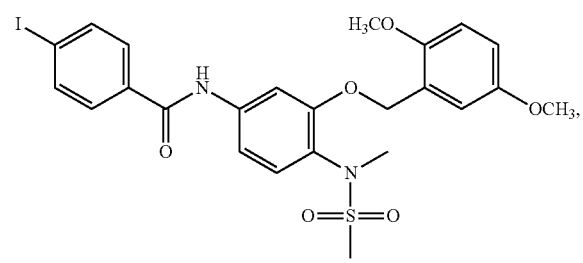

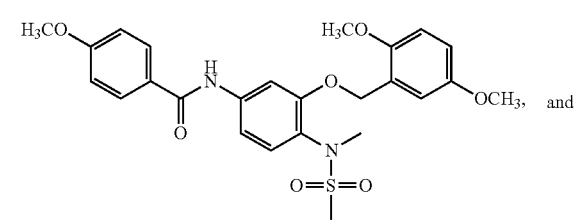

and

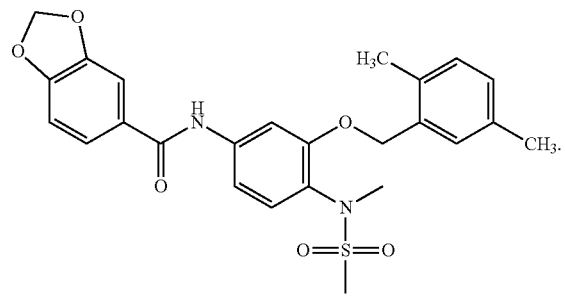

A further aspect of the invention provides a method of treating a cancer, comprising administering to a mammal a therapeutically effective amount of a compound of formula (I) or a pharmaceutically acceptable salt thereof. Cancers that may be treated may be selected from cancers that are vulnerable to the interference of the calcium signal transduction in the cancer cells.

In various embodiments of the method, the cancer is selected from breast cancer, colon cancer, CNS cancer, leukemia, melanoma, non-small cell lung cancer, ovarian cancer, renal cancer, and prostate cancer.

In one embodiment, the invention relates to novel substituted benzamide derivatives of benzene-sulfonanilide antitumor agents which exhibit a very potent ability to inhibit cancer cell growth, thereby providing an effective strategy for cancer therapy. The term "derivative" is intended to encompass compounds which are structurally related to the compound of formula (I) or which possess substantially equivalent activity to the compound of formula (I). By way of example, such compounds may include, but are not limited to, esters, metabolic products, and prodrugs thereof. Such compounds can be formed in vivo, such as by metabolic mechanisms. In another embodiment, the invention relates to methods of using Compound #10 (Benzo[1,3]dioxole-5-carboxylic acid [3-(2,5-dimethyl-benzyloxy)-4-(methanesulfonyl-methyl-amino)-phenyl]-amide), compound #40 (N-[3-(2,5-dimethyl-benzyloxy)-4-(methanesulfonyl-methyl-amino)-phenyl]-4-iodo-benzamide), and compound #41 (N-[3-(2,5-dimethoxy-benzyloxy)-4-(methanesulfonyl-methyl-amino)-phenyl]-4-methoxy-benzamide) for treating cancers, including but not limited to, prostate cancer, breast cancer, leukemia, non-small cell lung cancer, colon cancer, CNS cancer, melanoma, ovarian cancer, renal cancer, bladder cancer, and lymphoma. For example, the compound of formula (I) for this purpose may be selected from:

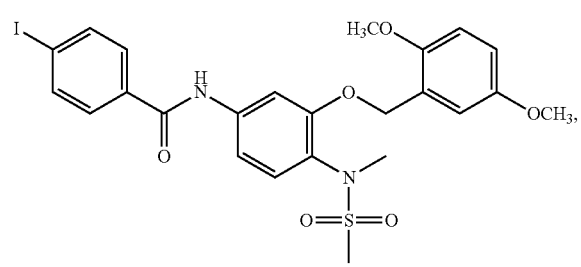

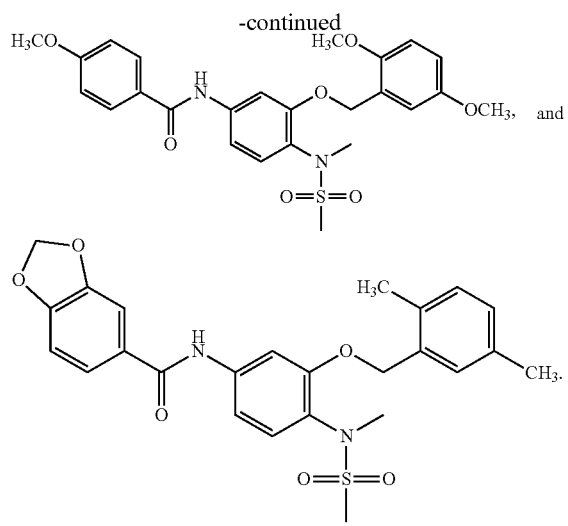

The compounds of formula (I) are useful in inhibiting growth of proliferative cells, including, but not limited to cancer cells. The compounds are further useful for treating, inhibiting, and delaying the onset of disorders characterized by unwanted, rapid cell proliferation, including but not limited to cancer, in mammals, and especially in humans. Cancers that these compounds work particularly well against include, but are not limited to prostate cancer, breast cancer, leukemia, non-small cell lung cancer, colon cancer, CNS cancer, melanoma, ovarian cancer, renal cancer, bladder cancer, lymphoma, and breast cancer. The compounds of formula (I) may be administered to a subject experiencing undesirable cell proliferation. Furthermore, the compounds of formula (I) may be administered to individuals with pre-cancers, as well as individuals prone to these disorders, for the prevention of these cancers.

The term "treatment" as used herein includes partial or total destruction of the undesirable proliferating cells with minimal destructive effects on normal cells.

The term "prevention" includes either preventing the onset of a clinically evident unwanted cell proliferation altogether, or preventing the onset of a pre-clinically evident stage of unwanted rapid cell proliferation, in individuals at risk. Also intended to be encompassed by this definition is the prevention of metastasis of malignant cells or to arrest or reverse the progression of malignant cells. This includes prophylactic treatment of those at risk of developing pre-cancers and cancers.

The term "subject" for purposes of treatment includes any human or animal who has a disorder characterized by unwanted, rapid cell proliferation or is at risk of developing such a disorder. Such disorders include, but are not limited to cancers and pre-cancers. For methods described herein, the subject is any human or animal, and in some embodiments, the subject is a human who has developed or is at risk of developing a disorder characterized by unwanted, rapid cell proliferation, such as cancer. A subject that is genetically predisposed to disorders characterized by unwanted, rapid cell proliferation may be at risk due to exposure to carcinogenic agents. Besides being useful for human treatment, the compounds of the present invention are also useful for veterinary treatment of mammals, including companion animals and farm animals, such as, but not limited to dogs, cats, horses, cows, sheep, and pigs.

The terms "proliferative cells", "proliferating cells", "rapidly proliferating cells", "undesirable proliferating cells", "undesirable rapidly proliferating cells", "unwanted rapidly proliferating cells", and the like, refer to cancer cells, pre-cancer cells, and other abnormal, rapidly dividing cells in a subject.

The compounds of formula (I) are useful in adjunct therapy. The phrase "adjunct therapy" (or "combination therapy"), when used to define use of a compound of the present invention, and one or more other pharmaceutical agents, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

The present invention may adopt any known methods of administering to a mammal a therapeutically effective amount of a compound of formula (I) or a pharmaceutically acceptable salt thereof. For intravenous, intramuscular, subcutaneous, or intraperitoneal administration, the compound may be combined with a sterile aqueous solution which is, in some embodiments, isotonic with the blood of the recipient. Such formulations may be prepared by dissolving solid active ingredient in water containing physiologically compatible substances such as sodium chloride, glycine, and the like, and having a buffered pH compatible with physiological conditions, to produce an aqueous solution, and rendering said solution sterile. The formulations may be present in unit or multi-dose containers such as sealed ampoules or vials.

For oral administration, the pharmaceutical composition may be in the form of, for example, a tablet, a capsule, a suspension or a liquid. In some embodiments, the pharmaceutical composition is made in the form of a dosage unit containing a particular amount of the active ingredient. Examples of such dosage units are capsules, tablets, powders, granules or suspensions, optionally with one or more conventional additives, such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

The terms "therapeutically effective" and "pharmacologically effective" are intended to qualify the amount of each agent which will achieve the goal of improvement in disease severity and the frequency of incidence of treatment of each agent by itself, while avoiding adverse side effects typically associated with alternative therapies.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, the particular compound employed, and the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg in some embodiments, and in the range of about 0.5 to 500 mg in other embodiments.

EXAMPLES

Chemicals were commercially available and used as received without further purification unless otherwise noted. Moisture sensitive reactions were carried out under a dry argon atmosphere in flame-dried glassware. Solvents were distilled before use under argon. Thin-layer chromatography was performed on precoated silica gel F254 plates (Whatman). Silica gel column chromatography was performed using silica gel 60A (Merck, 230-400 Mesh). All the NMR spectra were recorded on a Varian 400 MHz in either DMSO-d6 or $CDCl_3$ Chemical shifts ($\delta$) for $^1$H NMR spectra are reported in parts per million to residual solvent protons.

Example 1

General procedure for the preparation of amine intermediates (N-[4-Amino-2-(2,5-disubstituted-benzyloxy)-phenyl]-N-methyl-methanesulfonamide)

A mixture of ferric chloride (4 mmol, 4 eq) and nitrobenzene intermediate (1 mmol, 1 eq) was added to a solvent mixture of dimethyl formamide and water (6:1, 7 mL). It was stirred for 30 min and then zinc dust (10 mmol, 10 eq) was added slowly. After completion of the reaction (10 min, monitored by TLC), the reaction mixture was filtered by passing through a celite pad. The filtrate was diluted with water and basified by adding saturated aqueous $Na_2CO_3$. The precipitated solid was collected by filtration and dried, and then it was dissolved in acetone. After filtering out the non soluble residues, the desired compound was recovered by distillation of the acetone under reduced pressure.

Example 2

General Procedure for the Preparation of $R_3$ Moiety Substituted Compounds from Amine Intermediates $K_2CO_3$ (5 mmol, 5 eq) and substituted acyl chloride (1.2 mmol, 1.2 eq) were successively added to a solution of amine compound (1.0 mmol, 1.0 eq) in dry 1, 4 dioxane and the mixture was stirred at room temperature overnight. After being cooled, 10 mL $H_2O$ and 3 mL saturated aqueous $Na_2CO_3$ were added to the mixture and it was stirred at room temperature over night. The precipitated solid was collected by filtration and washed with $H_2O$ and cold ethyl ether/hexane to afford the desired compounds.

Example 3

N-[3-(2,5-Dimethyl-benzyloxy)-4-(methanesulfonyl-methyl-amino)-phenyl]-4-nitro-benzamide (Compound #1)

4-Nitro-benzoyl chloride was used and it was stirred at room temperature over night. Pale yellow solid, yield 88%: $^1$H-NMR (400 MHz, DMSO-d$_6$) $\delta$ 10.68 (1H, s), 8.41 (2H, d, J=8.0 Hz), 8.21 (2H, d, J=8.2 Hz), 7.75 (1H, s), 7.44 (1H, d, J=8.4 Hz), 7.33 (2H, m), 7.15 (1H, d, J=7.8 Hz), 7.09 (1H, d, J=7.8 Hz), 5.11 (2H, s), 3.12 (3H, s), 2.88 (3H, s), 2.32 (3H, s), 2.28 (3H, s); HRMS calculated for $C_{24}H_{26}N_2NaO_4S$ (M+Na)$^+$ 461.1511. Found 461.1511.

Example 4

N-[3-(2,5-Dimethyl-benzyloxy)-4-(methanesulfonyl-methyl-amino)-phenyl]-3-nitro-benzamide (Compound #2)

3-Nitro-benzoyl chloride was used and it was stirred at room temperature over night. White solid, yield 86%: $^1$H-NMR (400 MHz, DMSO-d$_6$) $\delta$ 10.70 (1H, s), 8.80 (1H, s), 8.48 (1H, d, J=8.0 Hz), 8.43 (1H, d, J=8.0 Hz), 7.89 (1H, dd, J=7.8, 7.8 Hz), 7.75 (1H, s), 7.45 (1H, d, J=8.6 Hz), 7.34 (2H, m), 7.15 (1H, d, J=7.4 Hz), 7.09 (1H, d, J=7.5 Hz), 5.12 (2H, s), 3.12 (3H, s), 2.88 (3H, s), 2.33 (3H, s), 2.28 (3H, s).

Example 5

4-Chloro-N-[3-(2,5-dimethyl-benzyloxy)-4-(methanesulfonyl-methyl-amino)-phenyl]-3-nitro-benzamide (Compound #3)

4-Chloro-3-nitro-benzoyl chloride was used and it was stirred at room temperature over night. White solid, yield 82%: $^1$H-NMR (400 MHz, DMSO-d$_6$) $\delta$ 10.65 (1H, s), 8.65 (1H, s), 8.28 (1H, d, J=8.4 Hz), 8.01 (1H, d, J=8.4 Hz), 7.72 (1H, s), 7.42 (1H, d, J=8.4 Hz), 7.33 (2H, m), 7.15 (1H, d, J=7.7 Hz), 7.09 (1H, d, J=7.4 Hz), 5.11 (2H, s), 3.12 (3H, s), 2.87 (3H, s), 2.32 (3H, s), 2.28 (3H, s).

Example 6

3,4-Dichloro-N-[3-(2,5-dimethyl-benzyloxy)-4-(methanesulfonyl-methyl-amino)-phenyl]-benzamide (Compound #4)

3,4-Dichloro-benzoyl chloride was used and it was stirred at room temperature over night. White solid, yield 69%: $^1$H-NMR (400 MHz, DMSO-d$_6$) $\delta$ 10.51 (1H, s), 8.23 (1H, s), 7.97 (1H, d, J=8.4 Hz), 7.85 (1H, d, J=8.4 Hz), 7.73 (1H, s), 7.42 (1H, d, J=7.6 Hz), 7.31 (2H, m), 7.15 (1H, d, J=7.7 Hz), 7.09 (1H, d, J=7.6 Hz), 5.10 (2H, s), 3.12 (3H, s), 2.87 (3H, s), 2.32 (3H, s), 2.28 (3H, s).

Example 7

Naphthalene-2-carboxylic acid [3-(2,5-dimethyl-benzyloxy)-4-(methanesulfonyl-methyl-amino)-phenyl]-amide (Compound #5)

Naphthalene-2-carbonyl chloride was used and it was stirred at room temperature for three days. White solid, yield 72%: $^1$H-NMR (400 MHz, DMSO-d$_6$) $\delta$ 10.56 (1H, s), 8.60 (1H, s), 8.12 (4H, m), 7.82 (1H, s), 7.67 (2H, m), 7.50 (1H, d, J=8.5 Hz), 7.33 (2H, m), 7.16 (1H, d, J=7.8 Hz), 7.10 (1H, d, J=7.3 Hz), 5.13 (2H, s), 3.13 (3H, s), 2.88 (3H, s), 2.34 (3H, s), 2.29 (3H, s).

Example 8

Biphenyl-4-carboxylic acid [3-(2,5-dimethyl-benzyloxy)-4-(methanesulfonyl-methyl-amino)-phenyl]-amide (Compound #6)

Biphenyl-4-carbonyl chloride was used and it was stirred at room temperature for three days. White solid, yield 73%:

¹H-NMR (400 MHz, DMSO-d₆) δ 10.42 (1H, s), 8.09 (2H, d, J=7.9 Hz), 7.88 (2H, d, J=7.8 Hz), 7.81 (1H, s), 7.79 (2H, d, J=7.2 Hz), 7.54 (4H, m), 7.33 (2H, m), 7.16 (1H, d, J=7.7 Hz), 7.10 (1H, d, J=7.5 Hz), 5.12 (2H, s), 3.12 (3H, s), 2.87 (3H, s), 2.33 (3H, s), 2.28 (3H, s).

Example 9

4-Cyano-N-[3-(2,5-dimethyl-benzyloxy)-4-(methanesulfonyl-methyl-amino)-phenyl]-benzamide (Compound #7)

4-Cyano-benzoyl chloride was used and it was stirred at room temperature over night. White solid, yield 75%: ¹H-NMR (400 MHz, DMSO-d₆) δ 10.60 (1H, s), 8.13 (2H, d, J=8.4 Hz), 8.06 (2H, d, J=8.2 Hz), 7.75 (1H, d, J=1.7 Hz), 7.43 (1H, dd, J=1.9, 8.5 Hz), 7.32 (2H, m), 7.15 (1H, d, J=7.7 Hz), 7.09 (1H, d, J=7.7 Hz), 5.11 (2H, s), 3.12 (3H, s), 2.87 (3H, s), 2.32 (3H, s), 2.28 (3H, s).

Example 10

3-Cyano-N-[3-(2,5-dimethyl-benzyloxy)-4-(methanesulfonyl-methyl-amino)-phenyl]-benzamide (Compound #8)

3-Cyano-benzoyl chloride was used and it was stirred at room temperature over night. White solid, yield 71%: ¹H-NMR (400 MHz, DMSO-d₆) δ 10.54 (1H, s), 8.42 (1H, s), 8.27 (1H, d, J=7.8 Hz), 8.10 (1H, d, J=7.7 Hz), 7.80 (2H, m), 7.43 (1H, d, J=8.5 Hz), 7.32 (2H, m), 7.15 (1H, d, J=7.7 Hz), 7.09 (1H, d, J=7.8 Hz), 5.11 (2H, s), 3.12 (3H, s), 2.87 (3H, s), 2.32 (3H, s), 2.28 (3H, s).

Example 11

4-Bromo-N-[3-(2,5-dimethyl-benzyloxy)-4-(methanesulfonyl-methyl-amino)-phenyl]-benzamide (Compound #9)

4-Bromo-benzoyl chloride was used and it was stirred at room temperature over night. White solid, yield 80%: ¹H-NMR (400 MHz, DMSO-d₆) δ 10.43 (1H, s), 7.93 (2H, d, J=8.2 Hz), 7.79 (2H, d, J=8.5 Hz), 7.75 (1H, s), 7.40 (1H, m), 7.31 (2H, m), 7.15 (1H, d, J=7.7 Hz), 7.09 (1H, d, J=7.7 Hz), 5.10 (2H, s), 3.11 (3H, s), 2.87 (3H, s), 2.32 (3H, s), 2.28 (3H, s).

Example 12

Benzo[1,3]dioxole-5-carboxylic acid [3-(2,5-dimethyl-benzyloxy)-4-(methanesulfonyl-methyl-amino)-phenyl]-amide (Compound #10)

1,3-Dihydro-isobenzofuran-5-carbonyl chloride was used and it was stirred at room temperature over night. White solid, yield 71%: ¹H-NMR (400 MHz, DMSO-d₆) δ 10.18 (1H, s), 7.75 (1H, s), 7.60 (1H, d, J=8.1 Hz), 7.52 (1H, s), 7.41 (1H, dd, J=1.5, 8.4 Hz), 7.31 (1H, s), 7.28 (1H, d, J=8.5 Hz), 7.15 (1H, d, J=7.6 Hz), 7.09 (2H, d, J=8.0 Hz), 5.09 (2H, s), 3.11 (3H, s), 2.86 (3H, s), 2.32 (3H, s), 2.28 (3H, s).

Example 13

N-[3-(2,5-Dimethyl-benzyloxy)-4-(methanesulfonyl-methyl-amino)-phenyl]-3,4,5-trimethoxy-benzamide (Compound #11)

3,4,5-Trimethoxy-benzoyl chloride was used and it was stirred at room temperature over night. White solid, yield 93%: ¹H-NMR (400 MHz, DMSO-d₆) δ 10.26 (1H, s), 7.76 (1H, s), 7.36 (5H, m), 7.13 (1H, d, J=7.7 Hz), 7.09 (1H, d, J=7.7 Hz), 5.11 (2H, s), 3.89 (6H, s), 3.75 (3H, s), 3.12 (3H, s), 2.87 (3H, s), 2.32 (3H, s), 2.28 (3H, s).

Example 14

N-[3-(2,5-Dimethyl-benzyloxy)-4-(methanesulfonyl-methyl-amino)-phenyl]-propionamide (Compound #12)

Propionoyl chloride was used and it was stirred at room temperature over night. White solid, yield 88%: ¹H-NMR (400 MHz, DMSO-d₆) δ 10.00 (1H, s), 7.58 (1H, s), 7.28 (1H, s), 7.23 (1H, d, J=8.5 Hz), 7.16 (1H, s), 7.14 (1H, d, J=7.6 Hz), 7.08 (1H, d, J=7.6 Hz), 5.06 (2H, s), 3.08 (3H, s), 2.84 (3H, s), 2.36 (2H, dd, J=7.5, 6.4 Hz), 2.30 (3H, s), 2.27 (3H, s), 1.10 (3H, dd, J=7.5, 7.6 Hz).

Example 15

Hexadecanoic acid [3-(2,5-dimethyl-benzyloxy)-4-(methanesulfonyl-methyl-amino)-phenyl]-amide (Compound #13)

Hexadecanoyl chloride was used and it was stirred at room temperature over night. White solid, yield 98%: ¹H-NMR (400 MHz, DMSO-d₆) δ 10.03 (1H, s), 7.59 (1H, s), 7.28 (1H, s), 7.20 (4H, m), 5.06 (2H, s), 3.08 (3H, s), 2.84 (3H, s), 2.30 (3H, s), 2.27 (3H, s), 1.58 (2H, br), 1.23 (26H, br), 0.87 (3H, dd, J=5.1, 6.6 Hz).

Example 16

2,4-Dichloro-N-[3-(2,5-dimethyl-benzyloxy)-4-(methanesulfonyl-methyl-amino)-phenyl]-benzamide (Compound #14)

2,4-Dichloro-benzoyl chloride was used and it was stirred at room temperature over night. White solid, yield 80%: ¹H-NMR (400 MHz, DMSO-d₆) δ 10.68 (1H, s), 7.79 (1H, s), 7.61 (1H, s), 7.64 (1H, d, J=8.2 Hz), 7.59 (1H, d, J=8.4 Hz), 7.29 (3H, br), 7.14 (1H, d, J=7.4 Hz), 7.08 (1H, d, J=7.4 Hz), 5.09 (2H, s), 3.12 (3H, s), 2.87 (3H, s), 2.31 (3H, s), 2.27 (3H, s).

Example 17

N-[3-(2,5-Dimethyl-benzyloxy)-4-(methanesulfonyl-methyl-amino)-phenyl]-3-trifluoromethyl-benzamide (Compound #15)

3-Trifluoromethyl-benzoyl chloride was used and it was stirred at room temperature over night. White solid, yield 93%: ¹H-NMR (400 MHz, DMSO-d₆) δ 10.61 (1H, s), 8.30 (2H, m), 8.00 (1H, d, J=7.6 Hz), 7.81 (2H, m), 7.44 (1H, d, J=8.5 Hz), 7.32 (1H, s), 7.32 (1H, d, J=8.4 Hz), 7.15 (1H, d, J=7.6 Hz), 7.09 (1H, d, J=7.6 Hz), 5.11 (2H, s), 3.12 (3H, s), 2.87 (3H, s), 2.32 (3H, s), 2.28 (3H, s).

Example 18

N-[3-(2,5-dimethyl-benzyloxy)-4-(methanesulfonyl-methyl-amino)-phenyl]-3,4-dimethoxy-benzamide (Compound #16)

3,4-Dimethoxy-benzoyl chloride was used and it was stirred at room temperature over night. White solid, yield 93%: ¹H-NMR (400 MHz, CDCl$_3$) δ 8.025 (2H, m), 7.510 (1H, J=2 Hz), 7.434 (1H, dd, J=8.4, 2 Hz), 7.309 (1H, J=8.8 Hz), 7.162 (1H, s), 7.109 (2H, m), 6.919 (1H, d, J=8.4 Hz), 6.832 (1H, dd, J=2, 8.4 Hz), 5.067 (2H, s), 3.957 (3H, s), 3.952 (3H, s), 3.195 (3H, s), 2.707 (3H, s), 2.335 (3H, s), 2.320 (3H, s).

Example 19

N-[3-(2,5-dimethyl-benzyloxy)-4-(methanesulfonyl-methyl-amino)-phenyl]-(3,4-dimethoxyphenyl)-acetamide (Compound #17)

(3,4-Dimethoxy-phenyl)-acetyl chloride was used and it was stirred at room temperature over night. White solid, yield 95%: ¹H-NMR (400 MHz, CDCl$_3$) δ 7.844 (1H, d, J=2.4 Hz), 7.240 (2H, m), 7.141 (1H, s), 7.103 (2H, m), 6.893 (2H, m), 6.825 (1H, d, J=1.6 Hz), 6.555 (1H, dd, J=2.4, 8.4 Hz), 5.029 (2H, s), 3.907 (3H, s), 3.898 (3H, s), 3.696 (2H, s), 3.157 (3H, s) 2.683 (3H, s), 2.322 (3H, s), 2.312 (3H, s).

Example 20

N-[3-(2,5-dimethyl-benzyloxy)-4-(methanesulfonyl-methyl-amino)-phenyl]-4-methoxy-benzamide (Compound #18)

4-Methoxy-benzoyl chloride was used and it was stirred at room temperature over night. White solid, yield 96%: ¹H-NMR (400 MHz, CDCl$_3$) δ 8.022 (1H, d, J=2.4 Hz), 7.864 (3H, m), 7.330 (1H, d, J=8.4 Hz), 7.175 (1H, s), 7.113 (2H, m), 6.995 (2H, m), 6.823 (1H, dd, J=2.4, 8.4 Hz), 5.086 (2H, s), 3.886 (3H, s), 3.198 (3H, s), 2.712 (3H, s), 2.345 (3H, s), 2.325 (3H, s).

Example 21

N-[3-(2,5-dimethyl-benzyloxy)-4-(methanesulfonyl-methyl-amino)-phenyl]-2-methoxy-benzamide (Compound #19)

2-Methoxy-benzoyl chloride was used and it was stirred at room temperature over night. White solid, yield 97%: ¹H-NMR (400 MHz, CDCl$_3$) δ 9.932 (1H, s), 8.283 (1H, dd, J=2, 8 Hz), 8.202 (1H, d, J=2.4 Hz), 7.535 (1H, m), 7.342 (1H, d, J=8.4 Hz), 7.106 (5H, m), 6.759 (1H, dd, J=2, 8.4 Hz), 5.119 (2H, s), 4.079 (3H, s), 3.201 (3H, s), 2.706 (3H, s), 2.361 (3H, s), 2.329 (3H, s).

Example 22

N-[3-(2,5-dimethyl-benzyloxy)-4-(methanesulfonyl-methyl-amino)-phenyl]-3-methoxy-benzamide (Compound #20)

3-Methoxy-benzoyl chloride was used and it was stirred at room temperature over night. White solid, yield 91%: ¹H-NMR (400 MHz, CDCl$_3$) δ 8.021 (1H, d, J=2.4 Hz), 7.938 (1H, s), 7.445 (1H, m), 7.406 (2H, m), 7.344 (1H, d, J=8.4 Hz), 7.177 (1H, s), 7.121 (3H, m), 6.848 (1H, dd, J=2.4, 8.4 Hz), 5.093 (2H, s), 3.885 (3H, s), 3.201 (3H, s), 2.714 (3H, s), 2.349 (3H, s), 2.327 (3H, s).

Example 23

N-[3-(2,5-dimethyl-benzyloxy)-4-(methanesulfonyl-methyl-amino)-phenyl]-3-methoxy-2,4,5-trifluorobenzamide (Compound #21)

3-Methoxy-2,4,5-trifluorobenzoyl chloride was used and it was stirred at room temperature over night. White solid, yield 98%: ¹H-NMR (400 MHz, CDCl$_3$) δ 8.381 (1H, d, J=14.8 Hz), 7.927 (1H, s), 7.680 (1H, m), 7.362 (1H, d, J=8.4 Hz), 7.180 (1H, s), 7.115 (2H, m), 6.880 (1H, d, J=8.4 Hz), 5.094 (2H, s), 4.106 (3H, s), 3.199 (3H, s), 2.719 (3H, s), 2.358 (3H, s), 2.328 (3H, s).

Example 24

N-[3-(2,5-dimethyl-benzyloxy)-4-(methanesulfonyl-methyl-amino)-phenyl]-2-ethyl-butyramide (Compound #22)

2-Ethyl-butyryl chloride was used and it was stirred at room temperature over night. White solid, yield 96%: ¹H-NMR (400 MHz, CDCl$_3$) δ 8.049 (1H, d, J=2.4 Hz), 7.296 (1H, s), 7.275 (1H, s), 7.157 (1H, s), 7.108 (2H, m), 6.673 (1H, dd, J=2.4, 8.8 Hz), 5.064 (2H, s), 3.172 (3H, s), 2.691 (3H, s), 2.339 (3H, s), 2.318 (3H, s), 2.08 (1H, m), 1.70 (4H, m), 0.970 (6H, t, J=7.6 Hz).

Example 25

N-[3-(2,5-dimethyl-benzyloxy)-4-(methanesulfonyl-methyl-amino)-phenyl]-cyclopentanecarboxamide (Compound #23)

Cyclopentane carbonyl chloride was used and it was stirred at room temperature over night. White solid, yield 93%: ¹H-NMR (400 MHz, CDCl$_3$) δ 7.998 (1H, d, J=2 Hz), 7.357 (1H, s), 7.265 (1H, d, J=8.4 Hz), 7.149 (1H, s), 7.106 (2H, m), 6.641 (1H, dd, J=2.4, 8.4 Hz), 5.045 (2H, s), 3.169 (3H, s), 2.703 (1H, m), 2.690 (3H, s), 2.327 (3H, s), 2.318 (3H, s), 1.921 (4H, m), 1.80 (2H, m), 1.641 (2H, m).

Example 26

N-[3-(2,5-dimethyl-benzyloxy)-4-(methanesulfonyl-methyl-amino)-phenyl]-2-phenyl-acetamide (Compound #24)

Phenylacetyl chloride was used and it was stirred at room temperature over night. White solid, yield 99%: ¹H-NMR (400 MHz, CDCl$_3$) δ 7.867 (1H, d, J=2.4 Hz), 7.399 (5H, m), 7.239 (1H, d, J=8.4 Hz), 7.187 (1H, s), 7.102 (3H, m), 6.535 (1H, dd, J=3, 9 Hz), 5.026 (2H, s), 3.757 (2H, s), 3.156 (3H, s), 2.679 (3H, s), 2.320 (3H, s), 2.312 (3H, s).

Example 27

N-[3-(2,5-dimethyl-benzyloxy)-4-(methanesulfonyl-methyl-amino)-phenyl]-1-naphthalenecarboxyamide (Compound #25)

1-Naphthoyl chloride was used and it was stirred at room temperature over night. White solid, yield 83%: ¹H-NMR (400 MHz, CDCl$_3$) δ 8.350 (1H, d, J=8 Hz), 8.105 (1H, s), 7.992 (1H, d, J=8.4 Hz), 7.921 (1H, m), 7.865 (1H, s), 7.741 (1H, d, J=6.4 Hz), 7.543 (3H, m), 7.345 (1H, d, J=8.4 Hz), 7.199 (1H, s), 7.116 (2H, m), 6.845 (1H, dd, J=2, 8.4 Hz), 5.129 (2H, s), 3.208 (3H, s), 2.711 (3H, s), 2.365 (3H, s), 2.336 (3H, s).

Example 28

N-[3-(2,5-dimethyl-benzyloxy)-4-(methanesulfonyl-methyl-amino)-phenyl]-3,5-bis(trifluoromethyl)benzamide (Compound #26)

3,5-Bis(trifluoromethyl)benzoyl chloride was used and it was stirred at room temperature over night. White solid, yield 93%: $^1$H-NMR (400 MHz, CDCl$_3$) δ 8.348 (3H, s), 8.067 (1H, s), 7.892 (1H, s), 7.289 (1H, d, J=10.8 Hz), 7.173 (1H, s), 7.108 (2H, m), 6.908 (1H, d, J=8.4 Hz), 5.051 (2H, s), 3.193 (3H, s), 2.754 (3H, s), 2.342 (3H, s), 2.309 (3H, s).

Example 29

N-[3-(2,5-dimethyl-benzyloxy)-4-(methanesulfonyl-methyl-amino)-phenyl]-3-bromobenzamide (Compound #27)

3-Bromobenzoyl chloride was used and it was stirred at room temperature over night. White solid, yield 99%: $^1$H-NMR (400 MHz, CDCl$_3$) δ 8.022 (2H, m), 7.947 (1H, d, J=2.4 Hz)), 7.810 (1H, d, J=8 Hz), 7.698 (1H, d, J=8 Hz), 7.404 (1H, t, J=8 Hz), 7.320 (1H, d, J=8.4 Hz), 7.172 (1H, s), 7.114 (2H, m), 6.867 (1H, dd, J=2.4, 8.4 Hz), 5.072 (2H, s), 3.199 (3H, s), 2.726 (3H, s), 2.343 (3H, s), 2.322 (3H, s).

Example 30

N-[3-(2,5-dimethyl-benzyloxy)-4-(methanesulfonyl-methyl-amino)-phenyl]-4-chlorobenzamide (Compound #28)

4-Chloro-benzoyl chloride was used and it was stirred at room temperature over night. White solid, yield 99%: $^1$H-NMR (400 MHz, CDCl$_3$) δ 8.066 (2H, m), 7.955 (1H, d, J=2 Hz), 7.844 (2H, m), 7.503 (3H, m), 7.302 (1H, d, J=8.4 Hz), 7.167 (1H, s), 7.111 (2H, m), 6.840 (1H, dd, J=2.4, 8.4 Hz), 5.061 (2H, s), 3.198 (3H, s), 2.721 (3H, s), 2.337 (3H, s), 2.319 (3H, s).

Example 31

N-[3-(2,5-dimethyl-benzyloxy)-4-(methanesulfonyl-methyl-amino)-phenyl]-4-iodobenzamide (Compound #29)

4-Iodo-benzoyl chloride was used and it was stirred at room temperature over night. White solid, yield 96%: $^1$H-NMR (400 MHz, DMSO-d$_6$) δ 10.408 (1H, s), 7.939 (2H, m), 7.748 (3H, m), 7.398 (1H, dd, J=2.4, 8.8 Hz), 7.291 (2H, m), 7.124 (2H, m), 5.090 (2H, s), 3.105 (3H, s), 2.858 (3H, s), 2.311 (3H, s), 2.270 (3H, s).

Example 32

N-[3-(2,5-dimethyl-benzyloxy)-4-(methanesulfonyl-methyl-amino)-phenyl]-4-methylsulfanyl-benzamide (Compound #30)

4-Methylsulfanyl-benzoyl chloride was used and it was stirred at room temperature over night. White solid, yield 92%: $^1$H-NMR (400 MHz, CDCl$_3$) δ 8.017 (1H, d, J=2.4 Hz), 7.868 (1H, s), 7.799 (2H, m), 7.327 (3H, m), 7.177 (1H, s), 7.116 (3H, m), 6.834 (1H, dd, J=2, 8.4 Hz), 5.093 (2H, s), 3.200 (3H, s), 2.715 (3H, s), 2.543 (3H, s), 2.348 (3H, s), 2.326 (3H, s).

Example 33

N-[3-(2,5-dimethyl-benzyloxy)-4-(methanesulfonyl-methyl-amino)-phenyl]-4-dimethylamino-benzamide (Compound #31)

4-Dimethylamino-benzoyl chloride was used and it was stirred at room temperature over night. White solid, yield 66%: $^1$H-NMR (400 MHz, CDCl$_3$) δ 8.086 (1H, d, J=2.4 Hz), 7.823 (1H, s), 7.789 (2H, d, J=9.2 Hz), 7.321 (2H, d, J=8.4 Hz), 7.174 (1H, s), 7.110 (2H, m), 6.790 (1H, dd, J=2, 8.4 Hz), 6.720 (2H, d, J=9.2 Hz), 5.089 (2H, s), 3.194 (3H, s), 3.064 (6H, s), 2.703 (3H, s), 2.343 (3H, s), 2.324 (3H, s).

Example 34

N-[3-(2,5-dimethyl-benzyloxy)-4-(methanesulfonyl-methyl-amino)-phenyl]-4-ethoxy-benzamide (Compound #32)

4-Ethoxy-benzoyl chloride was used and it was stirred at room temperature over night. White solid, yield 70%: $^1$H-NMR (400 MHz, CDCl$_3$) δ 8.014 (1H, d, J=2 Hz), 7.925 (1H, s), 7.847 (2H, m), 7.316 (2H, d, J=8.4 Hz), 7.168 (1H, s), 7.110 (2H, m), 6.972 (2H, m), 6.822 (1H, dd, J=2.4, 8.4 Hz), 5.074 (2H, s), 4.111 (2H, q, J=7.2 Hz), 3.195 (3H, s), 2.708 (3H, s), 2.340 (3H, s), 2.320 (3H, s), 1.455 (3H, t, J=7.2 Hz).

Example 35

N-[3-(2,5-dimethyl-benzyloxy)-4-(methanesulfonyl-methyl-amino)-phenyl]-4-ethyl-benzamide (Compound #33)

4-Ethyl-benzoyl chloride was used and it was stirred at room temperature over night. Pale yellow solid, yield 64%: $^1$H-NMR (400 MHz, CDCl$_3$) δ 8.038 (1H, d, J=2.4 Hz), 7.987 (1H, s), 7.814 (2H, m), 7.327 (3H, m), 7.173 (1H, s), 7.112 (2H, m), 6.834 (1H, dd, J=2.4, 8.4 Hz), 5.083 (2H, s), 3.197 (3H, s), 2.733 (2H, q, J=7.6 Hz), 2.708 (3H, s), 2.343 (3H, s), 2.324 (3H, s), 1.276 (3H, t, J=7.6 Hz).

Example 36

N-[3-(2,5-dimethyl-benzyloxy)-4-(methanesulfonyl-methyl-amino)-phenyl]-4-trifluoromethyl-benzamide (Compound #34)

4-Trifluoromethyl-benzoyl chloride was used and it was stirred at room temperature over night. White solid, yield 84%: $^1$H-NMR (400 MHz, DMSO-d$_6$) δ 10.590 (1H, s), 8.157 (2H, d, J=8 Hz), 7.941 (2H, d, J=8 Hz), 7.753 (1H, d, J=2.4 Hz), 7.419 (1H, dd, J=2.4, 8.8 Hz), 7.307 (2H, m), 7.129 (2H, m), 5.107 (2H, s), 3.116 (3H, s), 2.871 (3H, s), 2.319 (3H, s), 2.275 (3H, s).

Example 37

N-[3-(2,5-dimethyl-benzyloxy)-4-(methanesulfonyl-methyl-amino)-phenyl]-4-trifluoromethoxy-benzamide (Compound #35)

4-Trifluoromethoxy-benzoyl chloride was used and it was stirred at room temperature over night. White solid, yield 79%: $^1$H-NMR (400 MHz, CDCl$_3$) δ 7.954 (4H, m), 7.350 (3H, m), 7.177 (1H, s), 7.117 (2H, m), 7.848 (1H, dd, J=2.4, 8.4 Hz), 5.088 (2H, s), 3.204 (3H, s), 2.724 (3H, s), 2.349 (3H, s), 2.324 (3H, s).

Example 38

N-[3-(2,5-dimethyl-benzyloxy)-4-(methanesulfonyl-methyl-amino)-phenyl]-4-methyl-benzamide (Compound #36)

4-Methyl-benzoyl chloride was used and it was stirred at room temperature over night. White solid, yield 69%: $^1$H-NMR (400 MHz, CDCl$_3$) δ 8.032 (1H, d, J=2 Hz), 7.956 (1H, s), 7.786 (2H, m), 7.339 (1H, s), 7.309 (2H, d, J=7.6 Hz), 7.175 (1H, s), 7.113 (2H, m), 6.834 (1H, dd, J=2, 8.4 Hz), 5.084 (2H, s), 3.198 (3H, s), 2.710 (3H, s), 2.438 (3H, s), 2.344 (3H, s), 2.324 (3H, s).

Example 39

N-[3-(2,5-dimethyl-benzyloxy)-4-(methanesulfonyl-methyl-amino)-phenyl]-furan-2-carboxamide (Compound #37)

2-Furoyl chloride was used and it was stirred at room temperature over night. White solid, yield 66%: $^1$H-NMR (400 MHz, CDCl$_3$) δ8.159 (1H, s), 8.004 (1H, d, J=2.4 Hz), 7.551 (1H, m), 7.352 (1H, d, J=8.4 Hz), 7.268 (1H, m), 7.180 (1H, s), 7.119 (2H, m), 6.875 (1H, dd, J=2.4, 8.8 Hz), 6.595 (1H, dd, J=2, 3.6 Hz), 5.091 (2H, s), 3.202 (3H, s), 2.720 (3H, s), 2.351 3H, s), 2.328 (3H, s).

Example 40

N-[3-(2,5-dimethyl-benzyloxy)-4-(methanesulfonyl-methyl-amino)-phenyl]-thiophene-2-carboxamide (Compound #38)

2-Thiophene carbonyl chloride was used and it was stirred at room temperature over night. White solid, yield 72%: $^1$H-NMR (400 MHz, CDCl$_3$) δ 7.986 (1H, d, J=2.4 Hz), 7.877 (1H, s), 7.668 (1H, dd, J=1.2, 3.6 Hz), 7.589 (1H, dd, J=1.2, 5.2 Hz), 7.323 (1H, d, J=8.4 Hz), 7.144 (4H, m), 6.816 (1H, dd, J=2.4, 8.8 Hz), 5.072 (2H, s), 3.197 (3H, s), 2.718 (3H, s), 2.341 (3H, s), 2.324 (3H, s).

Example 41

N-[3-(2,5-dimethyl-benzyloxy)-4-(methanesulfonyl-methyl-amino)-phenyl]-isoxazole-5-carboxamide (Compound #39)

Isoxazole-5-carbonyl chloride was used and it was stirred at room temperature over night. White solid, yield 99%: $^1$H-NMR (400 MHz, CDCl$_3$) δ 8.418 (1H, d, J=2 Hz), 8.360 (1H, s), 7.849 (1H, dd, J=2.4 Hz), 7.391 (1H, d, J=8.4 Hz), 7.181 (1H, s), 7.126 (2H, m), 7.060 (1H, d, J=2 Hz), 7.005 (1H, dd, J=2.4, 8.4 Hz), 5.095 (2H, s), 3.211 (3H, s), 2.741 (3H, s), 2.357 (3H, s), 2.329 (3H, s).

The synthesis reactions for compounds #1-39 in Examples 3-41 are illustrated in the following:

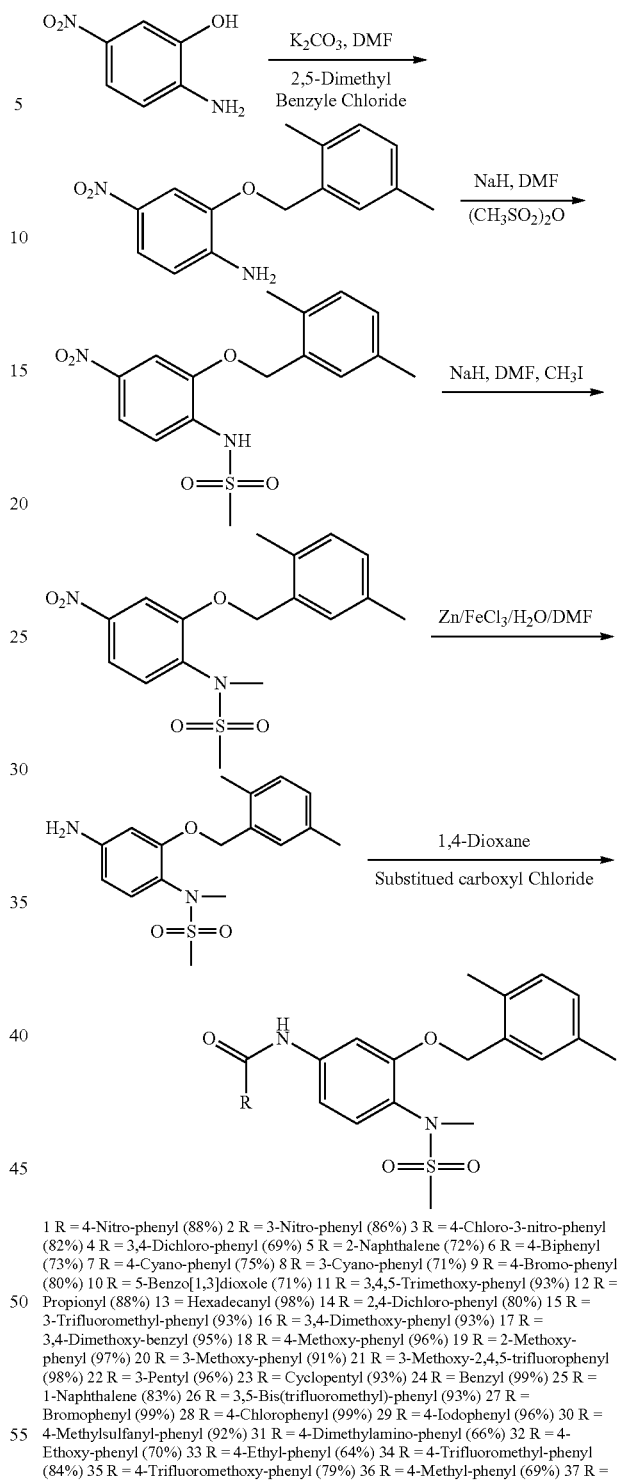

1 R = 4-Nitro-phenyl (88%) 2 R = 3-Nitro-phenyl (86%) 3 R = 4-Chloro-3-nitro-phenyl (82%) 4 R = 3,4-Dichloro-phenyl (69%) 5 R = 2-Naphthalene (72%) 6 R = 4-Biphenyl (73%) 7 R = 4-Cyano-phenyl (75%) 8 R = 3-Cyano-phenyl (71%) 9 R = 4-Bromo-phenyl (80%) 10 R = 5-Benzo[1,3]dioxole (71%) 11 R = 3,4,5-Trimethoxy-phenyl (93%) 12 R = Propionyl (88%) 13 = Hexadecanyl (98%) 14 R = 2,4-Dichloro-phenyl (80%) 15 R = 3-Trifluoromethyl-phenyl (93%) 16 R = 3,4-Dimethoxy-phenyl (93%) 17 R = 3,4-Dimethoxy-benzyl (95%) 18 R = 4-Methoxy-phenyl (96%) 19 R = 2-Methoxy-phenyl (97%) 20 R = 3-Methoxy-phenyl (91%) 21 R = 3-Methoxy-2,4,5-trifluorophenyl (98%) 22 R = 3-Pentyl (96%) 23 R = Cyclopentyl (93%) 24 R = Benzyl (99%) 25 R = 1-Naphthalene (83%) 26 R = 3,5-Bis(trifluoromethyl)-phenyl (93%) 27 R = Bromophenyl (99%) 28 R = 4-Chlorophenyl (99%) 29 R = 4-Iodophenyl (96%) 30 R = 4-Methylsulfanyl-phenyl (92%) 31 R = 4-Dimethylamino-phenyl (66%) 32 R = 4-Ethoxy-phenyl (70%) 33 R = 4-Ethyl-phenyl (64%) 34 R = 4-Trifluoromethyl-phenyl (84%) 35 R = 4-Trifluoromethoxy-phenyl (79%) 36 R = 4-Methyl-phenyl (69%) 37 R = 2-Furyl (66%) 38 R = 2-Thiophene (72%) 39 R = 5-Isoxazole (99%)

Example 42

N-[3-(2,5-dimethoxyl-benzyloxy)-4-(methanesulfonyl-methyl-amino)-phenyl]-4-iodo-benzamide (Compound #40

4-Iodobenzoyl chloride was used and it was stirred at room temperature for overnight. White solid, yield 62%: $^1$H-NMR (400 MHz, CDCl₃) δ 7.940 (1H, s), 7.872 (3H, m), 7.608 (2H, m), 7.323 (1H, d, J=8.4 Hz), 7.011 (1H, d, J=2.8 Hz), 6.879 (1H, d, J=2.4 Hz), 6.854 (2H, m), 5.127 (2H, s), 3.782 (3H, s), 3.778 (3H, s), 3.232 (3H, s), 2.814 (3H, s).

Example 43

N-[3-(2,5-dimethoxy-benzyloxy)-4-(methanesulfonyl-methyl-amino)-phenyl]-4-methoxy-benzamide (Compound #41)

4-Methoxybenzoyl chloride was used and it was stirred at room temperature for overnight. White solid, yield 60%: ¹H-NMR (400 MHz, CDCl3) δ 7.932 (1H, d, J=2.4 Hz), 7.863 (3H, m), 7.327 (1H, d, J=8.4 Hz), 7.004 (3H, m), 6.853 (3H, m), 5.138 (2H, s), 3.886 (3H, s), 3.782 (6H, s), 3.232 (3H, s), 2.807 (3H, s).

Example 44

N-[3-(2,5-dimethoxy-benzyloxy)-4-(methanesulfonyl-methyl-amino)-phenyl]-4-bromobenzamide (Compound #42)

4-Bromobenzoyl chloride was used and it was stirred at room temperature for overnight. White solid, yield 91%: ¹H-NMR (400 MHz, CDCl3) δ 7.933 (1H, s), 7.875 (1H, d, J=2 Hz), 7.759 (2H, m), 7.647 (2H, m), 7.327 (1H, d, J=8.4 Hz), 7.012 (1H, d, J=2.8 Hz), 6.882 (1H, d, J=2 Hz), 6.857 (2H, m), 5.130 (2H, s), 3.783 (3H, s), 3.779 (3H, s), 3.234 (3H, s), 2.816 (3H, s).

Example 45

N-[3-(2,5-dimethoxyl-benzyloxy)-4-(methanesulfonyl-methyl-amino)-phenyl]-1,3-benzodioxole-5-carboxamide (Compound #43)

Piperonyloyl chloride was used and it was stirred at room temperature for overnight. White solid, yield 66%: ¹H-NMR (400 MHz, CDCl₃) δ 7.890 (1H, d, J=2.4 Hz), 7.857 (1H, s), 7.412 (1H, dd, J=1.6, 8 Hz), 7.368 (1H, d, J=1.6 Hz), 7.318 (1H, d, J=8.4 Hz), 7.012 (1H, d, J=2.4 Hz), 6.891 (1H, d, J=8 Hz), 6.852 (3H, m), 6.070 (2H, s), 5.128 (2H, s), 3.781 (6H, s), 3.230 (3H, s), 2.810 (3H, s).

Example 46

N-[3-(2,5-dimethoxyl-benzyloxy)-4-(methanesulfonyl-methyl-amino)-phenyl]-3,4-dimethoxy-benzamide (Compound #44)

3,4-Dimethoxybenzoyl chloride was used and it was stirred at room temperature for overnight. White solid, yield 80%: 1H-NMR (400 MHz, CDCl3) δ 7.942 (1H, d, J=2.4 Hz), 7.925 (1H, s), 7.504 (1H, d, J=2 Hz), 7.411 (1H, dd, J=2, 8.4 Hz), 7.332 (1H, d, J=8.4 Hz), 7.016 (1H, d, J=2.4 Hz), 6.928 (1H, d, J=8.4 Hz), 6.861 (3H, m), 5.138 (2H, s), 3.968 (3H, s), 3.961 (3H, s), 3.783 (3H, s), 3.781 (3H, s), 3.236 (3H, s), 2.810 (3H, s).

Example 47

N-[3-(2,5-dimethoxyl-benzyloxy)-4-(methanesulfonyl-methyl-amino)-phenyl]-2-naphthalenecarboxamide (Compound #45)

2-Naphthoyl chloride was used and it was stirred at room temperature for overnight. White solid, yield 83%: 1H-NMR (400 MHz, CDCl3) δ 8.402 (1H, s), 8.153 (1H, s), 7.947 (5H, m), 7.607 (2H, m), 7.355 (1H, d, J=8.4 Hz), 7.028 (1H, d, J=2.8 Hz), 6.940 (1H, dd, J=2.4, 8.4 Hz), 6.855 (2H, m), 5.159 (2H, s), 3.786 (3H, s), 3.782 (3H, s), 3.248 (3H, s), 2.818 (3H, s).

The synthesis reactions for compounds #40-45 in Examples 42-47 are illustrated in the following:

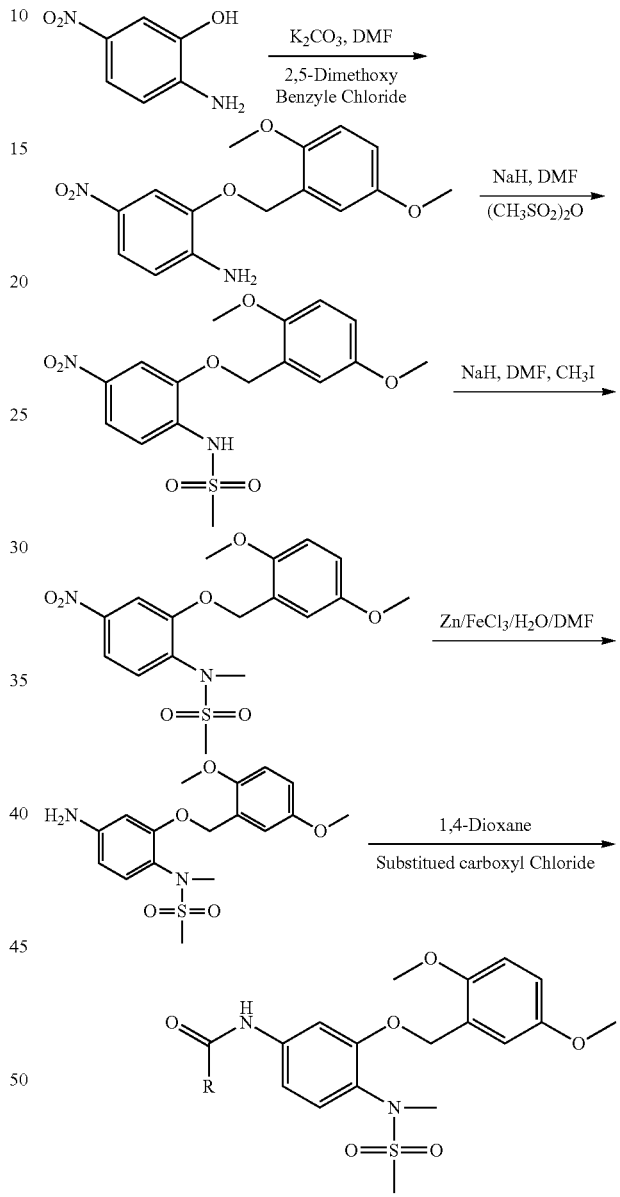

40 R = 4-Iodophenyl (62%) 41 R = 4-Methoxy-phenyl (60%) 42 R = 4-Bromophenyl (91%) 43 R = 3,4-methylenedioxy-phenyl (66%) 44 R = 3,4-Dimethoxy-phenyl (80%) 45 R = 2-Naphthalene (83%)

Example 48

N-[3-(2,5-dichloro-benzyloxy)-4-(methanesulfonyl-methyl-amino)-phenyl]-4-bromobenzamide (Compound #46)

4-Bromobenzoyl chloride was used and it was stirred at room temperature for overnight. White solid, yield 65%:

1H-NMR (400 MHz, CDCl3) δ 8.153 (1H, s), 7.795 (1H, s), 7.778 (2H, d, J=8.4 Hz), 7.635 (2H, d, J=8.4 Hz), 7.553 (1H, d, J=2 Hz), 7.365 (1H, d, J=8.4 Hz), 7.303 (2H, m), 6.946 (1H, dd, J=2, 8.8 Hz), 5.086 (2H, s), 3.252 (3H, s), 2.878 (3H, s).

Example 49

N-[3-(2,5-dichloro-benzyloxy)-4-(methanesulfonyl-methyl-amino)-phenyl]-4-methoxy-benzamide (Compound #47)

4-Methoxybenzoyl chloride was used and it was stirred at room temperature for overnight. White solid, yield 70%: 1H-NMR (400 MHz, CDCl3) δ 7.959 (1H, s), 7.919 (1H, d, J=2 Hz), 7.860 (2H, d, J=9.2 Hz), 7.550 (1H, d, J=2.4 Hz), 7.311 (3H, m), 6.988 (2H, d, J=8.8 Hz), 6.903 (1H, dd, J=2.4, 8.4 Hz), 5.164 (2H, s), 3.884 (3H, s), 3.249 (3H, s), 2.850 (3H, s).

Example 50

N-[3-(2,5-dichloro-benzyloxy)-4-(methanesulfonyl-methyl-amino)-phenyl]-3,4-dimethoxy-benzamide (Compound #48)

3,4-Dimethoxybenzoyl chloride was used and it was stirred at room temperature for overnight. White solid, yield 86%: 1H-NMR (400 MHz, CDCl3) δ 8.047 (1H, s), 7.925 (1H, d, J=2.4 Hz), 7.548 (1H, d, J=2.4 Hz), 7.502 (1H, d, J=2 Hz), 7.435 (1H, dd, J=2, 8.4 Hz), 7.334 (3H, m), 6.911 (2H, m), 5.152 (2H, s), 3.960 (3H, s), 3.955 (3H, s), 3.250 (3H, s), 2.858 (3H, s).

Example 51

N-[3-(2,5-dichloro-benzyloxy)-4-(methanesulfonyl-methyl-amino)-phenyl]-4-iodo-benzamide (Compound #49)

4-Iodobenzoyl chloride was used and it was stirred at room temperature for overnight. White solid, yield 85%: 1H-NMR (400 MHz, DMSO-d6) δ 7.941 (2H, m), 7.773 (1H, d, J=2.4 Hz), 7.745 (2H, m), 7.681 (1H, d, J=2.4 Hz), 7.593 (1H, d, J=8.4 Hz), 7.501 (1H, dd, J=2.8, 8.4 Hz), 7.464 (1H, dd, J=2.4, 8.4 Hz), 7.329 (1H, d, J=8.4 Hz), 5.215 (2H, s), 3.139 (3H, s), 2.931 (3H, s).

Example 52

N-[3-(2,5-dichloro-benzyloxy)-4-(methanesulfonyl-methyl-amino)-phenyl]-2-naphthalenecarboxamide (Compound #50)

2-Naphthoyl chloride was used and it was stirred at room temperature for overnight. White solid, yield 98%: ¹H-NMR (400 MHz, CDCl₃) δ 8.413 (1H, s), 8.264 (1H, s), 7.948 (5H, m), 7.579 (3H, m), 7.360 (2H, m), 7.291 (1H, dd, J=2.8, 8.8 Hz), 6.988 (1H, dd, J=2, 8.4 Hz), 5.164 (2H, s), 3.262 (3H, s), 2.861 (3H, s).

Example 53

N-[3-(2,5-dichloro-benzyloxy)-4-(methanesulfonyl-methyl-amino)-phenyl]-1,3-benzodioxole-5-carboxamide (Compound #51)

Piperonyloyl chloride was used and it was stirred at room temperature for over night. White solid, yield 84%: ¹H-NMR (400 MHz, CDCl₃) δ 7.953 (1H, s), 7.864 (1H, d, J=2.4 Hz), 7.548 (1H, d, J=2.4 Hz), 7.428 (1H, dd, J=1.6, 8 Hz), 7.370 (2H, m), 7.311 (2H, m), 6.898 (2H, m), 6.067 (2H, s), 5.143 (2H, s), 3.247 (3H, s), 2.860 (3H, s).

The synthesis reactions for compounds #46-51 in Examples 48-53 are illustrated in the following:

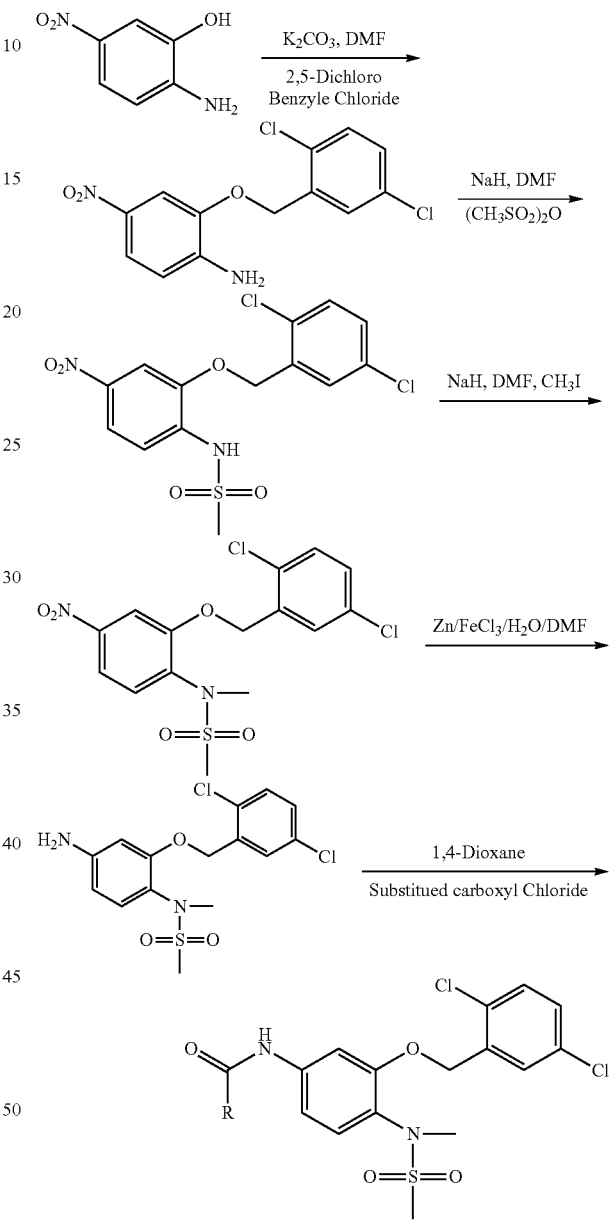

46 R = 4-Bromophenyl (65%) 47 R = 4-Methoxy-phenyl (70%) 48 R = 3,4-Dimethoxy-phenyl (86%) 49 R = 4-Iodophenyl (85%) 50 R = 2-Naphthalene (98%) 51 R = 3,4-methylenedioxy-phenyl (84%)

Example 54

N-[3-(2-methyl-5-trifluoromethyl-benzyloxy)-4-(methanesulfonyl-methyl-amino)-phenyl]-4-bromobenzamide (Compound #52)

4-Bromobenzoyl chloride was used and it was stirred at room temperature for overnight. White solid, yield 78%:

$^1$H-NMR (400 MHz, CDCl$_3$) δ 8.026 (2H, m), 7.759 (2H, m), 7.704 (1H, s), 7.653 (2H, m), 7.548 (1H, d, J=8 Hz), 7.365 (1H, d, J=8 Hz), 7.330 (1H, d, J=8.4 Hz), 6.835 (1H, dd, J=2.4, 8.4 Hz), 5.160 (2H, s), 3.228 (3H, s), 2.783 (3H, s), 2.457 (3H, s).

Example 55

N-[3-(2-methyl-5-trifluoromethyl-benzyloxy)-4-(methanesulfonyl-methyl-amino)-phenyl]-4-methoxy-benzamide (Compound #53)

4-methoxybenzoyl chloride was used and it was stirred at room temperature for overnight. White solid, yield 97%: $^1$H-NMR (400 MHz, CDCl$_3$) δ 8.081 (1H, d, J=2.4 Hz), 7.959 (1H, s), 7.860 (2H, m), 7.702 (1H, s), 7.543 (1H, d, J=8 Hz), 7.362 (1H, d, J=8 Hz), 7.330 (1H, d, J=8.8 Hz), 6.990 (2H, m), 6.815 (1H, dd, J=2, 8.4 Hz), 5.163 (2H, s), 3.883 (3H, s), 3.224 (3H, s), 2.770 (3H, s), 2.455 (3H, s).

Example 56

N-[3-(2-methyl-5-trifluoromethyl-benzyloxy)-4-(methanesulfonyl-methyl-amino)-phenyl]-3,4-dimethoxy-benzamide (Compound #54)

3,4-Dimethoxybenzoyl chloride was used and it was stirred at room temperature for overnight. White solid, yield 91%: $^1$H-NMR (400 MHz, CDCl$_3$) δ 8.087 (1H, s), 8.032 (1H, s), 7.707 (1H, s), 7.534 (2H, m), 7.432 (1H, d, J=8 Hz), 7.345 (2H, m), 6.922 (1H, d, J=8 Hz), 6.826 (1H, d, J=8.4 Hz), 5.161 (2H, s), 3.965 (3H, s), 3.955 (3H, s), 3.227 (3H, s), 2.775 (3H, s), 2.453 (3H, s).

Example 57

N-[3-(2-methyl-5-trifluoromethyl-benzyloxy)-4-(methanesulfonyl-methyl-amino)-phenyl]-4-iodo-benzamide (Compound #55)

4-Iodobenzoyl chloride was used and it was stirred at room temperature for overnight. White solid, yield 87%: $^1$H-NMR (400 MHz, CDCl$_3$) δ 8.064 (1H, s), 8.018 (1H, d, J=2.4 Hz), 7.855 (2H, d, J=8.4 Hz), 7.703 (1H, s), 7.616 (2H, d, J=8.8 Hz), 7.546 (1H, d, J=8.4 Hz), 7.363 (1H, d, J=7.6 Hz), 7.314 (1H, d, J=8.4 Hz), 6.833 (1H, dd, J=2.4, 8.4 Hz), 5.149 (2H, s), 3.225 (3H, s), 2.781 (3H, s), 2.451 (3H, s).

Example 58

N-[3-(2-methyl-5-trifluoromethyl-benzyloxy)-4-(methanesulfonyl-methyl-amino)-phenyl]-2-naphthalenecarboxamide (Compound #56)

4-Naphthoyl chloride was used and it was stirred at room temperature for overnight. White solid, yield 97%: $^1$H-NMR (400 MHz, DMSO-d$_6$) δ 10.580 (1H, s), 8.592 (1H, s), 8.070 (4H, m), 7.925 (1H, s), 7.833 (1H, d, J=2 Hz), 7.654 (3H, m), 7.506 (2H, m), 7.351 (1H, d, J=8.4 Hz), 5.264 (2H, s), 3.146 (3H, s), 2.909 (3H, s), 2.470 (3H, s).

Example 59

N-[3-(2-methyl-5-trifluoromethyl-benzyloxy)-4-(methanesulfonyl-methyl-amino)-phenyl]-1,3-benzodioxole-5-carboxamide (Compound #57)

Piperonyloyl chloride was used and it was stirred at room temperature for over night. White solid, yield 84%: $^1$H-NMR (400 MHz, CDCl$_3$) δ 8.032 (1H, s), 7.943 (1H, s), 7.701 (1H, s), 7.542 (1H, d, J=8 Hz), 7.371 (4H, m), 6.888 (1H, d, J=8 Hz), 6.812 (1H, d, J=8 Hz), 6.065 (2H, s), 5.153 (2H, s), 3.223 (3H, s), 2.780 (3H, s), 2.453 (3H, s).

The synthesis reactions for compounds #52-57 in Examples 54-59 are illustrated in the following:

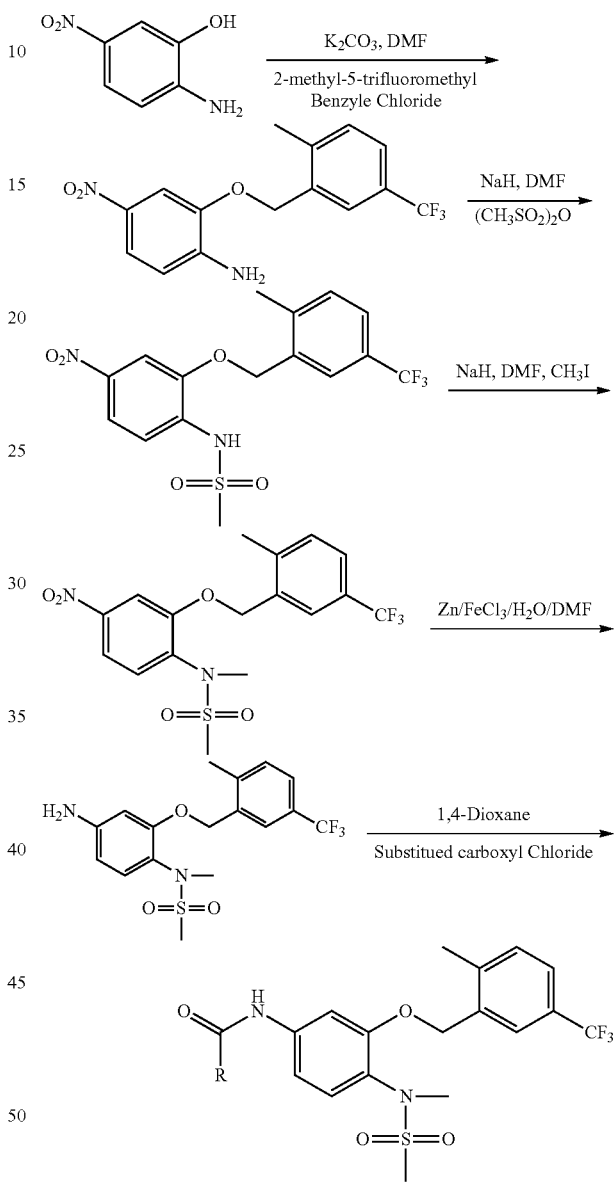

52 R = 4-Bromophenyl (78%) 53 R = 4-Methoxy-phenyl (97%) 54 R = 3,4-Dimethoxy-phenyl (91%) 55 R = 4-Iodophenyl (87%) 56 R = 2-Naphthalene (97%) 57 R = 3,4-methylenedioxy-phenyl (84%)

Example 60

Biological Evaluation of the Compounds

SKBR-3 cells were obtained from ATCC (Rockville, Md.). SKBR-3 cells were maintained in MEM custom media (MEM, Earle's salts, 1.5× amino acids, 2× non-essential amino acids, L-glutamine, 1.5× vitamins, Gibco BRL, Cleveland Clinic) supplemented with 10% bovine serum (BS), 2 mM L-glutamine, 100 U/mL penicillin-streptomycin. Bovine serum was heat inactivated for 30 min in a 56° C. water bath before use. Cell cultures were grown at 37° C., in a humidified atmosphere of 5% $CO_2$ in a Hereaus $CO_2$ incubator. For all experiments, cells were seeded in 96 well plates with 5000 cells/well density.

The effect of the compounds on cancer cell viability was assessed by using the 3-(4,5-dimethylthiazol-2-yl)-2,5-diphenyl-2H-tetrazolium bromide assay in six replicates with SKBR-3 cells. Cells were grown in custom medium in 96-well, flat-bottomed plates for 24 h, and were exposed to various concentrations of nimesulide derivatives dissolved in DMSO (final concentration≤0.1%) in media for different time intervals. Controls received DMSO vehicle at a concentration equal to that in drug-treated cells. The medium was removed, replaced by 200 μl of 0.5 mg/ml of 3-(4,5-dimethylthiazol-2-yl)-2,5-diphenyl-2H-tetrazolium bromide in fresh media, and cells were incubated in the $CO_2$ incubator at 37° C. for 2 h. Supernatants were removed from the wells, and the reduced 3-(4,5-dimethylthiazol-2-yl)-2,5-diphenyl-2H-tetrazolium bromide dye was solubilized in 200 μl/well DMSO. Absorbance at 570 nm was determined on a plate reader. The half maximal inhibitory concentrations ($IC_{50}$) of the compounds (#1-#45) are listed in Table 5.

TABLE 5

| Comp. Code | $IC_{50}$ |
| --- | --- |
| #1 | 1.13 ± 0.10 μM |
| #2 | 1.97 ± 0.21 μM |
| #3 | 3.35 ± 0.40 μM |
| #4 | 0.91 ± 0.05 μM |
| #5 | 0.21 ± 0.01 μM |
| #6 | 2.28 ± 0.09 μM |
| #7 | 1.46 ± 0.06 μM |
| #8 | 3.01 ± 0.12 μM |
| #9 | 0.22 ± 0.01 μM |
| #10 (NSC751382) | 0.20 ± 0.01 μM |
| #11 | 0.30 ± 0.02 μM |
| #12 | 43.27 ± 7.38 μM |
| #13 | 11.05 ± 4.76 μ |
| #14 | 0.80 ± 0.01 μM |
| #15 | 2.78 ± 0.29 μM |
| #16 | 0.19 ± 0.14 μM |
| #17 | 34.02 ± 20.14 μM |
| #18 | 0.15 ± 0.05 μM |
| #19 | 0.68 ± 0.32 μM |
| #20 | 6.88 ± 3.18 μM |
| #21 | 2.16 ± 1.08 μM |
| #22 | 51.24 ± 44.97 μM |
| #23 | 11.21 ± 4.47 μM |
| #24 | >100 μM |
| #25 | 3.95 ± 2.09 μM |
| #26 | 55.35 ± 41.08 μM |
| #27 | 7.34 ± 3.99 μM |
| #28 | 2.15 ± 0.94 μM |
| #29 | 0.13 ± 0.07 μM |
| #30 | 0.66 ± 0.32 μM |
| #31 | 1.01 ± 0.52 μM |
| #32 | 0.41 ± 0.03 μM |
| #33 | 2.48 ± 1.44 μM |
| #34 | 1.20 ± 0.59 μM |
| #35 | 0.58 ± 0.29 μM |
| #36 | 2.82 ± 1.51 μM |
| #37 | 16.65 ± 2.26 μM |
| #38 | 20.12 ± 5.28 μM |
| #39 | 21.88 ± 5.08 μM |
| #40 | 1.8 ± 0.7 nM |
| #41 | 0.87 ± 0.33 nM |
| #42 | 3.5 ± 1.9 nM |
| #43 | 7.5 ± 2.8 nM |
| #44 | 2.6 ± 1.3 nM |
| #45 | 16.6 ± 7.7 nM |

Example 61

Sixty Cancer Cell Lines Screening by National Cancer Institute Developmental Therapeutics Program (NCIDTP)

Three potent analogs (compound #10, compound #41, and compound #40) were studied by NCIDTP 60 cancer cell lines screening service.

FIGS. 1-9 show the dose responsive curves of leukemia, non-small cell lung cancer, colon cancer, CNS cancer, melanoma, ovarian cancer, renal cancer, prostate, and cancer breast cancer, respectively, to compound #10 under NCIDTP Experimental ID 0912NS69. The in-vitro testing results for compound #10 (known as NSC751382 in NCI) under NCIDTP Experimental ID 0912NS69 are tabulated in Table 6.

TABLE 6

National Cancer Institute Developmental Therapeutics Program
In-Vitro Testing Results

| NSC: 751382/1 | Experiment ID: 0912NS69 | Test Type: 08 | Units: Molar |
| --- | --- | --- | --- |
| Report Date: Jan. 28, 2010 | Test Date Dec. 14, 2009 | QNS: | MC: |
| COMI: CSUOH0901 (90857) | Stain Reagent: SRB Dual-Pass Related | SSPL: 0XRM | |

| | | Log10 Concentration | | | | | | | | | | | | |
| --- | --- | --- | --- | --- | --- | --- | --- | --- | --- | --- | --- | --- | --- | --- |
| | Time | Mean Optical Densities | | | | | Percent Growth | | | | | | | |
| Panel/Cell Line | Zero Ctrl | −8.0 | −7.0 | −6.0 | −5.0 | −4.0 | −8.0 | −7.0 | −6.0 | −5.0 | −4.0 | GI50 | TGI | LC50 |
| Leukemia | | | | | | | | | | | | | | |
| CCRF-CEM | 0.349 1.510 | 1.413 | 0.709 | 0.496 | 0.511 | 0.529 | 92 | 31 | 13 | 14 | 16 | 4.85E−8 | >1.00E−4 | >1.00E−4 |
| HL-60(TB) | 0.717 2.426 | 2.234 | 0.708 | 0.634 | 40.575 | 0.575 | 89 | −1 | −12 | −20 | −20 | 2.69E−8 | 9.67E−8 | >1.00E−4 |
| K-562 | 0.257 1.596 | 1.537 | 0.529 | 0.402 | 0.374 | 0.382 | 96 | 20 | 11 | 9 | 9 | 4.03E−8 | >1.00E−4 | >1.00E−4 |
| MOLT-4 | 0.598 1.869 | 1.854 | 1.364 | 0.746 | 0.688 | 0.761 | 99 | 80 | 12 | 7 | 13 | 1.63E−7 | >1.00E−4 | >1.00E−4 |
| RPMI-8226 | 0.685 1.958 | 1.871 | 1.712 | 0.867 | 0.672 | 0.764 | 93 | 81 | 14 | −2 | 6 | 2.90E−7 | | >1.00E−4 |

TABLE 6-continued

National Cancer Institute Developmental Therapeutics Program
In-Vitro Testing Results

Non-Small Cell Lung Cancer

| Cell Line | | | | | | | | | | | | | | |
|---|---|---|---|---|---|---|---|---|---|---|---|---|---|---|
| A549/ATCC | 0.353 | 1.337 | 1.305 | 1.141 | 0.475 | 0.396 | 0.250 | 97 | 80 | 12 | 5 | −29 | 2.78E−7 | 1.36E−5 | >1.00E−4 |
| EKVX | 0.633 | 1.637 | 1.580 | 1.515 | 1.026 | 0.888 | 0.964 | 94 | 88 | 39 | 25 | 33 | 5.98E−7 | >1.00E−4 | >1.00E−4 |
| HOP-62 | 0.259 | 0.791 | 0.802 | 0.707 | 0.355 | 0.357 | 0.359 | 102 | 84 | 18 | 18 | 19 | 3.29E−7 | >1.00E−4 | >1.00E−4 |
| HOP-92 | 1.146 | 1.669 | 1.553 | 1.470 | 1.469 | 1.349 | 1.339 | 78 | 62 | 62 | 39 | 37 | 3.22E−8 | >1.00E−4 | >1.00E−4 |
| NCI-H226 | 0.670 | 1.267 | 1.192 | 1.228 | 0.918 | 0.792 | 0.769 | 87 | 93 | 42 | 20 | 16 | 6.86E−7 | >1.00E−4 | >1.00E−4 |
| NCI-H23 | 0.402 | 1.315 | 1.286 | 0.969 | 0.444 | 0.426 | 0.425 | 97 | 62 | 5 | 3 | 2 | 1.62E−7 | >1.00E−4 | >1.00E−4 |
| NCI-H322M | 0.461 | 1.010 | 0.978 | 0.959 | 0.625 | 0.604 | 0.617 | 94 | 91 | 30 | 26 | 28 | 4.68E−7 | >1.00E−4 | >1.00E−4 |
| NCI-H460 | 0.241 | 1.615 | 1.548 | 1.229 | 0.216 | 0.218 | 0.184 | 95 | 72 | −11 | −10 | −24 | 1.84E−7 | 7.44E−7 | >1.00E−4 |
| NCI-H522 | 0.593 | 0.962 | 0.889 | 0.677 | 0.373 | 0.345 | 0.380 | 80 | 23 | −37 | −42 | −36 | 3.35E−8 | 2.40E−7 | >1.00E−4 |

Colon Cancer

| COLO 205 | 0.195 | 1.175 | 1.221 | 1.169 | 0.207 | 0.116 | 0.131 | 105 | 99 | 1 | −41 | −33 | 3.18E−7 | 1.07E−6 | >1.00E−4 |
|---|---|---|---|---|---|---|---|---|---|---|---|---|---|---|---|
| HCC-2998 | 0.747 | 1.962 | 1.954 | 1.450 | 0.450 | 0.288 | 0.266 | 99 | 58 | −40 | −61 | −64 | 1.20E−7 | 3.92E−7 | 2.97E−6 |
| HCT-116 | 0.239 | 1.480 | 1.338 | 0.792 | 0.244 | 0.127 | 0.126 | 89 | 45 | | −47 | −47 | 7.53E−8 | 1.02E−6 | >1.00E−4 |
| HCT-15 | 0.243 | 1.665 | 1.604 | 1.301 | 0.549 | 0.482 | 0.484 | 96 | 74 | 22 | 17 | 17 | 2.89E−7 | >1.00E−4 | >1.00E−4 |
| HT29 | 0.153 | 0.674 | 0.677 | 0.380 | 0.113 | 0.080 | 0.080 | 101 | 44 | −26 | −48 | −48 | 7.72E−8 | 4.19E−7 | >1.00E−4 |
| KM12 | 0.247 | 1.186 | 1.121 | 0.687 | 0.257 | 0.201 | 0.176 | 93 | 47 | 1 | −19 | −29 | 8.55E−8 | 1.13E−6 | >1.00E−4 |
| SW-620 | 0.205 | 1.010 | 0.942 | 0.620 | 0.361 | 0.377 | 0.335 | 92 | 52 | 19 | 21 | 16 | 1.12E−7 | >1.00E−4 | >1.00E−4 |

CNS Cancer

| SF-268 | 0.389 | 1.078 | 1.032 | 0.918 | 0.517 | 0.452 | 0.498 | 93 | 77 | 19 | 9 | 16 | 2.88E−7 | >1.00E−4 | >1.00E−4 |
|---|---|---|---|---|---|---|---|---|---|---|---|---|---|---|---|
| SF-295 | 0.751 | 2.229 | 2.105 | 1.486 | 0.656 | 0.633 | 0.638 | 92 | 50 | −13 | −16 | −15 | 9.83E−8 | 6.26E−7 | >1.00E−4 |
| SF-539 | 0.602 | 1.951 | 1.832 | 1.363 | 0.540 | 0.543 | 0.608 | 91 | 56 | −10 | −10 | | 1.25E−7 | | >1.00E−4 |
| SNB-19 | 0.492 | 1.521 | 1.452 | 1.403 | 0.860 | 0.804 | 0.890 | 93 | 89 | 36 | 30 | 39 | 5.37E−7 | >1.00E−4 | >1.00E−4 |
| SNB-75 | 0.519 | 0.952 | 0.893 | 0.912 | 0.494 | 0.487 | 0.534 | 86 | 91 | −5 | −6 | 3 | 2.66E−7 | | >1.00E−4 |
| U251 | 0.273 | 1.303 | 1.276 | 1.051 | 0.432 | 0.357 | 0.230 | 97 | 76 | 15 | 8 | −16 | 2.66E−7 | 2.19E−5 | >1.00E−4 |

Melanoma

| LOX IMVI | 0.105 | 0.700 | 0.645 | 0.351 | 0.184 | 0.233 | 0.263 | 91 | 41 | 13 | 21 | 26 | 6.66E−8 | >1.00E−4 | >1.00E−4 |
|---|---|---|---|---|---|---|---|---|---|---|---|---|---|---|---|
| MALME-3M | 0.844 | 1.470 | 1.389 | 1.224 | 1.038 | 1.096 | 1.152 | 87 | 61 | 31 | 40 | 49 | 2.29E−7 | >1.00E−4 | >1.00E−4 |
| M14 | 0.297 | 0.922 | 0.858 | 0.575 | 0.269 | 0.164 | 0.211 | 90 | 45 | −9 | −45 | −29 | 7.57E−8 | 6.69E−7 | >1.00E−4 |
| MDA-MB-435 | 0.349 | 1.325 | 1.276 | 0.336 | 0.244 | 0.250 | 0.289 | 95 | −4 | −30 | −28 | −17 | 2.85E−8 | 9.14E−8 | >1.00E−4 |
| SK-MEL-2 | 0.714 | 1.206 | 1.200 | 0.948 | 0.624 | 0.631 | 0.588 | 99 | 48 | −13 | −12 | −18 | 8.97E−8 | 8.16E−7 | >1.00E−4 |
| SK-MEL-28 | 0.451 | 1.244 | 1.170 | 1.111 | 0.798 | 0.836 | 0.846 | 91 | 83 | 44 | 49 | 50 | 6.92E−7 | >1.00E−4 | >1.00E−4 |
| SK-MEL-5 | 0.409 | 2.077 | 1.910 | 1.676 | 0.603 | 0.238 | 0.176 | 90 | 76 | 12 | −42 | −57 | 2.53E−7 | 1.65E−6 | 3.41E−5 |
| UACC-257 | 0.559 | 1.030 | 0.971 | 0.811 | 0.708 | 0.694 | 0.620 | 88 | 53 | 32 | 29 | 13 | 1.44E−7 | >1.00E−4 | >1.00E−4 |
| UACC-62 | 0.662 | 1.847 | 1.772 | 1.499 | 1.103 | 0.838 | 0.825 | 94 | 71 | 37 | 15 | 14 | 4.14E−7 | >1.00E−4 | >1.00E−4 |

Ovarian Cancer

| IGROV1 | 0.479 | 1.510 | 1.430 | 1.196 | 0.660 | 0.613 | 0.618 | 92 | 69 | 18 | 13 | 13 | 2.37E−7 | >1.00E−4 | >1.00E−4 |
|---|---|---|---|---|---|---|---|---|---|---|---|---|---|---|---|
| OVCAR-3 | 0.536 | 1.139 | 1.115 | 0.651 | 0.176 | 0.302 | 0.365 | 96 | 19 | −67 | −44 | −32 | 3.96E−8 | 1.66E−7 | |
| OVCAR-4 | 0.347 | 0.714 | 0.667 | 0.678 | 0.546 | 0.521 | 0.553 | 87 | 90 | 54 | 47 | 56 | | >1.00E−4 | >1.00E−4 |
| OVCAR-5 | 0.488 | 1.119 | 1.027 | 1.023 | 0.723 | 0.694 | 0.645 | 85 | 85 | 37 | 33 | 25 | 5.38E−7 | >1.00E−4 | >1.00E−4 |
| OVCAR-8 | 0.228 | 0.847 | 0.807 | 0.721 | 0.288 | 0.278 | 0.266 | 94 | 80 | 10 | 8 | 6 | 2.65E−7 | >1.00E−4 | >1.00E−4 |
| NCI/ADR-RES | 0.283 | 0.958 | 0.945 | 0.511 | 0.222 | 0.248 | 0.225 | 98 | 34 | −22 | −12 | −20 | 5.62E−8 | 4.07E−7 | >1.00E−4 |
| SK-OV-3 | 0.460 | 1.142 | 1.135 | 1.042 | 0.513 | 0.493 | 0.497 | 99 | 85 | 8 | 5 | 5 | 2.85E−7 | >1.00E−4 | >1.00E−4 |

Renal Cancer

| 786-0 | 0.387 | 1.328 | 1.239 | 1.038 | 0.397 | 0.304 | 0.331 | 91 | 69 | 1 | −22 | −14 | 1.91E−7 | 1.11E−6 | >1.00E−4 |
|---|---|---|---|---|---|---|---|---|---|---|---|---|---|---|---|
| A498 | 0.736 | 1.219 | 1.153 | 1.002 | 0.706 | 0.685 | 0.703 | 86 | 55 | −4 | −7 | −5 | 1.22E−7 | 8.53E−7 | >1.00E−4 |
| ACHN | 0.348 | 1.667 | 1.600 | 1.339 | 0.943 | 0.723 | 0.645 | 95 | 75 | 45 | 26 | 23 | 6.87E−7 | >1.00E−4 | >1.00E−4 |
| CAKI-1 | 0.678 | 1.750 | 1.751 | 1.255 | 0.852 | 0.703 | 0.729 | 100 | 54 | 16 | 2 | 5 | 1.26E−7 | >1.00E−4 | >1.00E−4 |
| RXF 393 | 0.649 | 0.855 | 0.815 | 0.774 | 0.393 | 0.519 | 0.532 | 81 | 61 | −39 | −20 | −18 | 1.28E−7 | 4.03E−7 | >1.00E−4 |
| SN12C | 0.519 | 1.708 | 1.663 | 1.606 | 0.875 | 0.778 | 0.796 | 96 | 91 | 30 | 22 | 23 | 4.72E−7 | >1.00E−4 | >1.00E−4 |
| TK-10 | 0.374 | 0.702 | 0.676 | 0.664 | 0.435 | 0.394 | 0.404 | 92 | 88 | 18 | 6 | 9 | 3.54E−7 | >1.00E−4 | >1.00E−4 |
| UO-31 | 0.569 | 1.217 | 1.072 | 1.039 | 0.795 | 0.647 | 0.859 | 78 | 73 | 35 | 12 | 14 | 3.95E−7 | >1.00E−4 | >1.00E−4 |

Prostate Cancer

| PC-3 | 0.397 | 1.398 | 1.317 | 0.812 | 0.607 | 0.594 | 0.603 | 92 | 41 | 21 | 20 | 21 | 6.77E−8 | >1.00E−4 | >1.00E−4 |
|---|---|---|---|---|---|---|---|---|---|---|---|---|---|---|---|
| DU-145 | 0.309 | 0.961 | 0.932 | 0.779 | 0.195 | 0.190 | 0.223 | 96 | 72 | −37 | −39 | −28 | 1.59E−7 | 4.57E−7 | >1.00E−4 |

Breast Cancer

| MCF7 | 0.204 | 1.271 | 1.190 | 0.769 | 0.374 | 0.310 | 0.281 | 92 | 53 | 16 | 10 | 7 | 1.20E−7 | >1.00E−4 | >1.00E−4 |
|---|---|---|---|---|---|---|---|---|---|---|---|---|---|---|---|
| MDA-MB-231/ATCC | 0.449 | 1.050 | 0.991 | 0.969 | 0.436 | 0.373 | 0.419 | 90 | 87 | −3 | −17 | −7 | 2.56E−7 | 9.26E−7 | >1.00E−4 |
| HS 578T | 0.514 | 0.999 | 0.950 | 0.744 | 0.490 | 0.469 | 0.527 | 90 | 47 | −5 | −9 | 3 | 8.70E−8 | | >1.00E−4 |
| BT-549 | 0.792 | 1.389 | 1.342 | 1.211 | 1.064 | 0.872 | 0.917 | 92 | 70 | 45 | 13 | 21 | 6.56E−7 | >1.00E−4 | >1.00E−4 |
| T-47D | 0.443 | 1.108 | 1.035 | 0.953 | 0.740 | 0.637 | 0.624 | 89 | 77 | 45 | 29 | 27 | 6.82E−7 | >1.00E−4 | >1.00E−4 |
| MDA-MB-468 | 0.536 | 1.176 | 1.082 | 1.002 | 0.280 | 0.283 | 0.234 | 85 | 73 | −48 | −47 | −56 | 1.55E−7 | 4.01E−7 | 1.99E−5 |

The one dose mean graphs of compound #41 on 60 cancer cells lines obtained from NCIDTP Experimental ID 1007OS83 are tabulated in Table 7.

Table 7
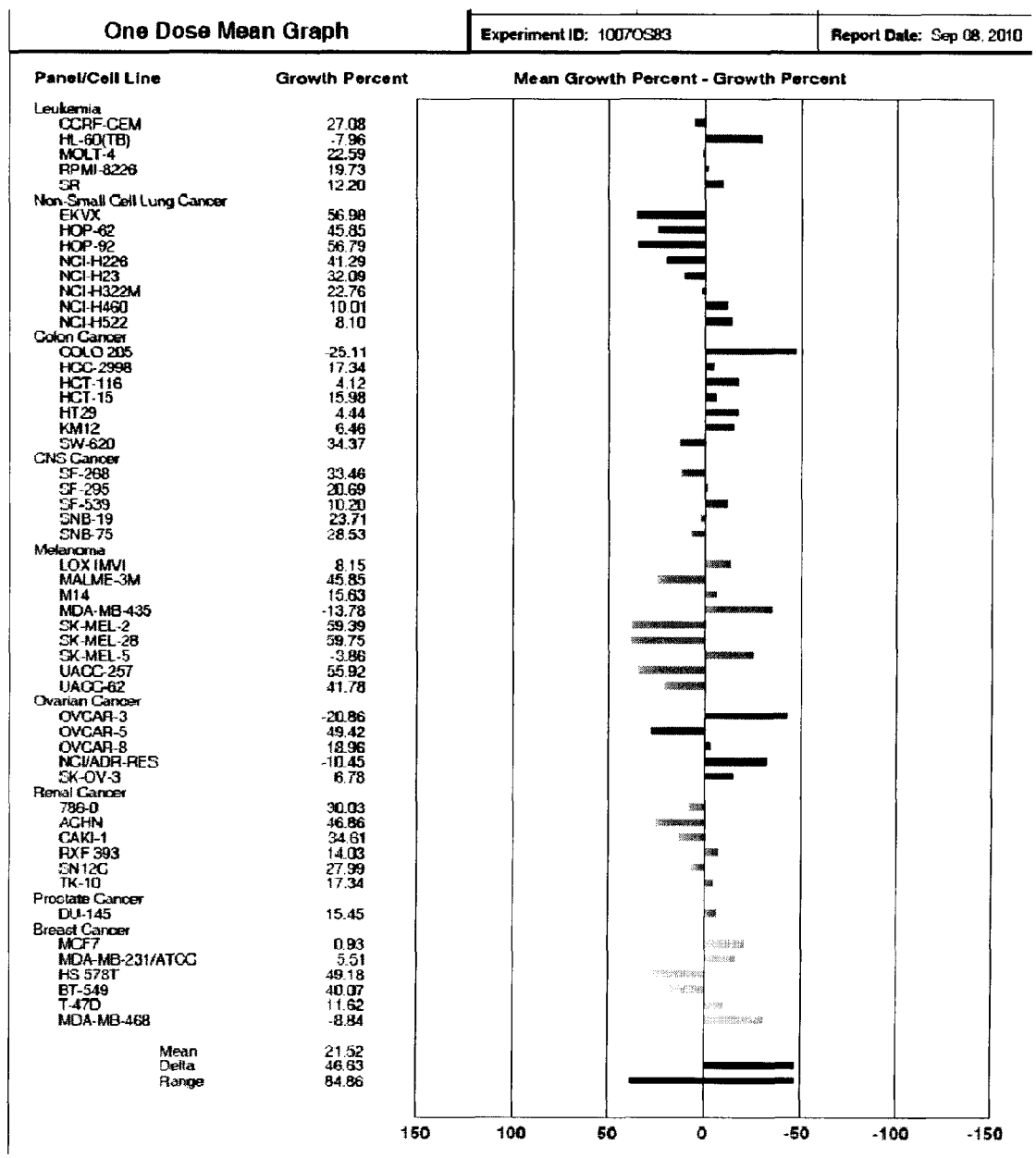

The one dose mean graphs of compound #40 on 60 cancer cells lines obtained from NCIDTP Experimental ID 1007OS83 are tabulated in Table 8.

Table 8
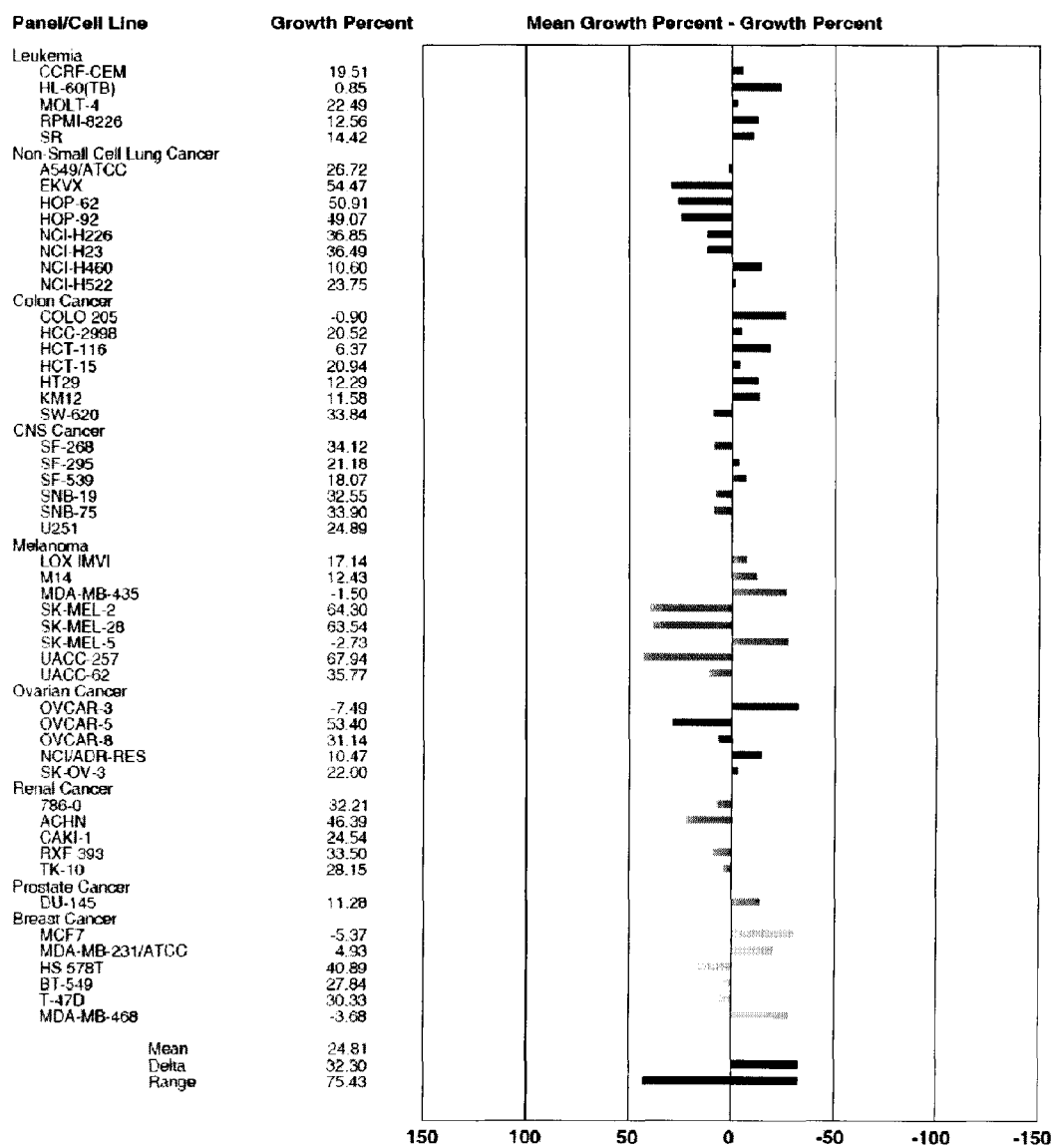

Example 62

Primary Mechanism Studies

Figure 10:
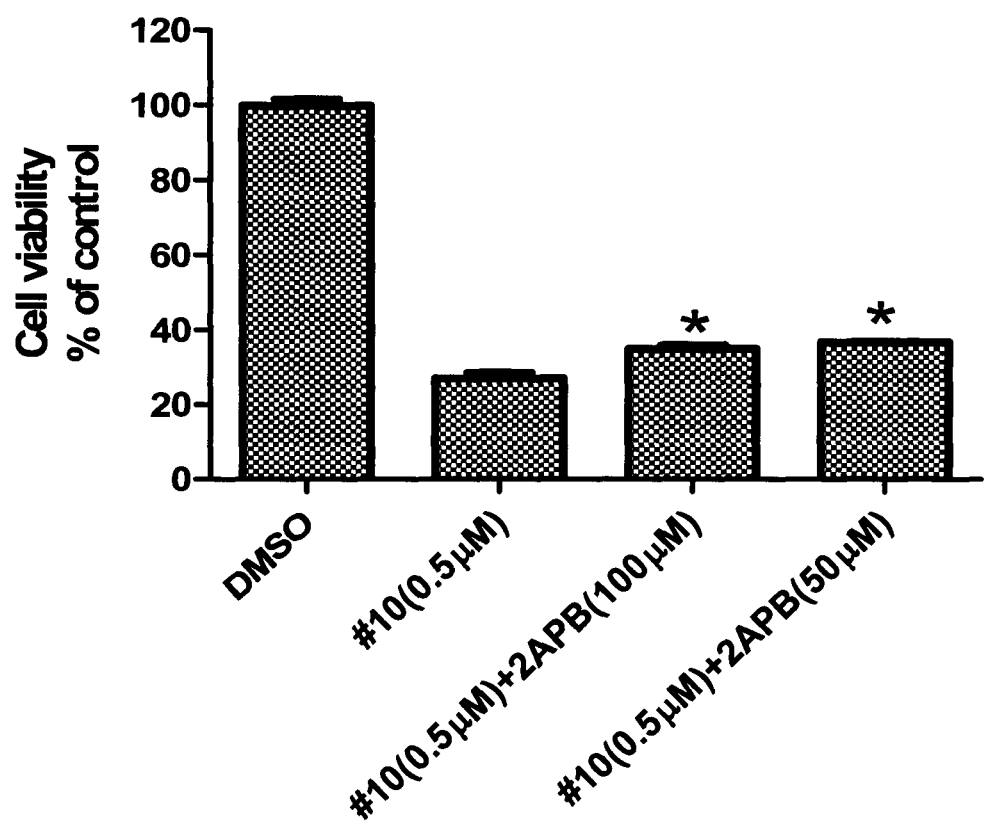
FIG. 10 shows the cell viability of control upon treatment of DMSO, a compound of formula (I) only, and different mixtures of the compound of formula (I) with 2-aminoethoxydiphenyl borate (2-APB) in accord with an embodiment of the invention.

A study on 2-aminoethoxydiphenyl borate (2-APB), a blocker of the endoplasmic reticulum calcium channel (inositol-1,4,5-trisphosphate receptor, IP3R), has demonstrated that it can partially rescue the cell death from compound #10 treatment. FIG. 10 shows the cell viability of control upon treatment of DMSO, compound #10 only, and different mixtures of compound #10 and 2-APB. The result in FIG. 10 suggests that compound #10 induces cell death that is at least partially related with calcium signal in the cells. For the experiment, 2-APB was first added. After two hours, different concentrations of compound #10 were added. The control cells were treated with same amount of DMSO to carry the drugs. The cell viability was evaluated after 48 hours.

Example 63

In Vivo Study

Figure 11:
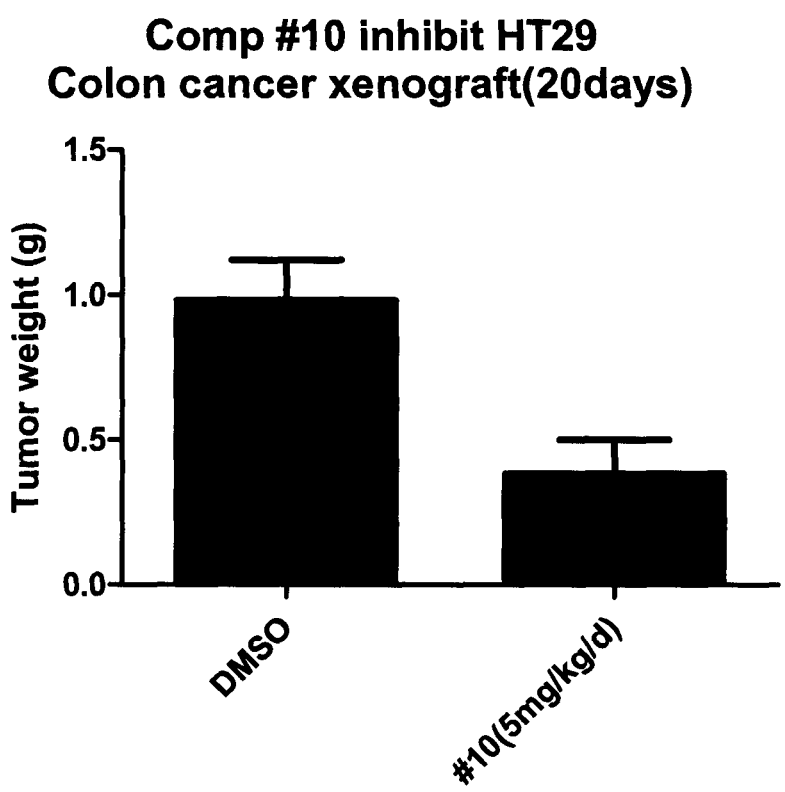
FIG. 11 shows the inhibition of a compound of formula (I) against HT29 colon cancer xenograft (20 days) in accord with an embodiment of the invention.

Based on the NCI screening results, at least compound #10 is very potent to inhibit the growth of many types of cancer cell including HT29 colon cancer cells. HT29 colon cancer xenograft model is a generally accepted in vivo cancer model and the formed tumor grows very aggressively. The model was thus used to evaluate the in vivo activity of compound #10, and the result is shown in FIG. 11. Compound #10 at 5 mg/kg/day dosage significantly inhibited the tumor growth, which proves that the compound is also active in vivo. In the experiment, HT29 xenografts were established in ovariectomized 5- to 6-week-old BALB/c athymic nude mice (Case Western Reserve University animal facility). When tumors reach 150-200 mm$^3$ (i.e., in 2-4 weeks), the animals are randomly allocated (n=3 per group) to be treated with the compounds or vehicle (1% Tween 80) administered via i.p. Tumor growth was assessed and tumor weights were measured at the end of the experiment after the mice were killed. The animal care was in accordance with institutional guidelines.

Due to high solubility, compounds such as compound #10 may have short half life in vivo. More hydrophobic analogs such as the compound of formula (II) may be produced to decrease the solubility, to increase the volume of distribution in vivo, and to increase the half life.

The exemplary embodiments have been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A compound of formula (I):

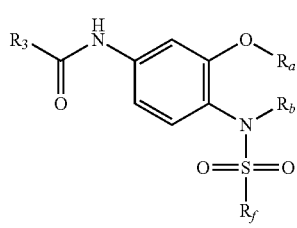

(I)

wherein $R_a$ is

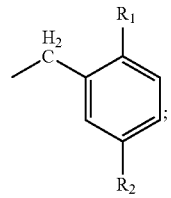

$R_1$ and $R_2$ are independently of each other selected from alkoxy groups; $R_b$ is selected from H and alkyl groups; $R_f$ is an alkyl; and $R_3$ is selected from:

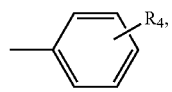

wherein $R_4$ is selected from halo, phenyl, substituted phenyl, and alkoxy;

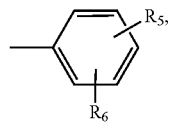

wherein $R_5$ and $R_6$ are independently of each other selected from alkoxy groups; and

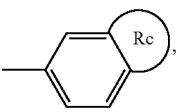

wherein Rc is selected from a fused ring, fused rings, and any bivalent carbon- or hetero-cyclic group.

2. The compound according to claim 1, wherein $R_b$ is methyl, $R_f$ is methyl, $R_1$ is methoxy, and $R_2$ is methoxy.

3. The compound according to claim 2, wherein $R_3$ is selected from:

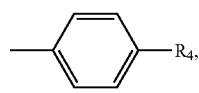

wherein $R_4$ is selected from Br, I, and OCH$_3$;

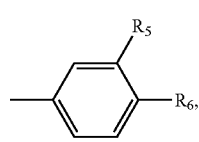

wherein $R_5$ and $R_6$ are both OCH$_3$;

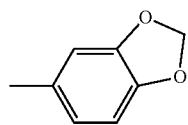

(3,4-(methylenedioxy)phenyl); and

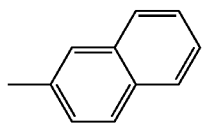

(napthyl such as 2-napthyl).

4. A compound of formula (I):

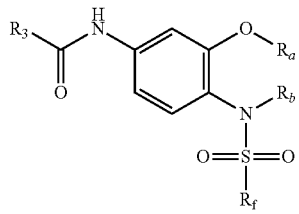
(I)

wherein $R_a$ is

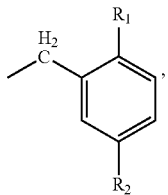

$R_1$ and $R_2$ are independently of each other selected from alkyl groups; $R_b$ is selected from H and alkyl groups; $R_f$ is an alkyl; and $R_3$ is selected from heterocyclic group, a phenyl group which is mono-, di-, or tri-substituted with alkoxy, alkylthio, and halo-substituted alkoxy, and

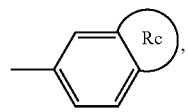

wherein Rc is selected from any bivalent carbon or heterocyclic group.

5. The compound according to claim 4, wherein $R_b$, $R_f$, $R_1$, and $R_2$ are all methyl.

6. The compound according to claim 5, wherein $R_3$ is selected from:

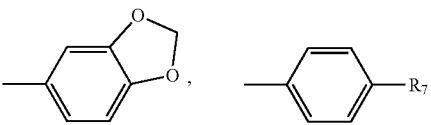

(wherein $R_7$ is —OCH$_3$, —OCH$_2$CH$_3$, —SCH$_3$, and —OCF$_3$),

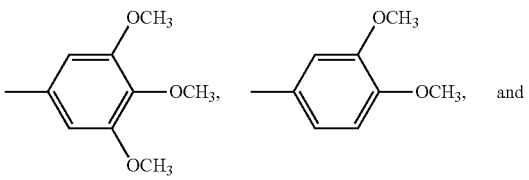

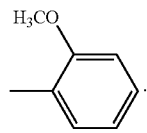

7. A compound of formula (I):

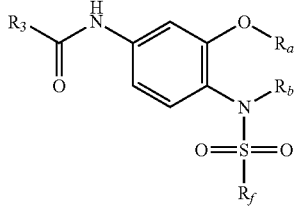
(I)

wherein $R_a$ is

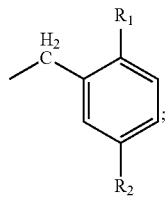

$R_1$ and $R_2$ are independently of each other selected from alkyl groups; $R_b$ is selected from H and alkyl groups; $R_f$ is an alkyl; and $R_3$ is heterocyclic group.

8. The compound according to claim 7, wherein $R_b$, $R_f$, $R_1$ and $R_2$ are all methyl.

9. The compound according to claim 8, wherein $R_3$ is selected from

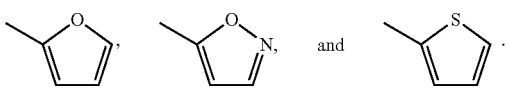

10. A compound of formula (I):

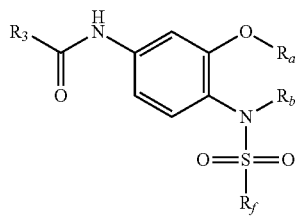

wherein $R_a$ is

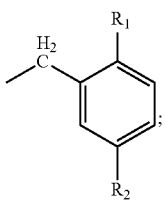

$R_1$ and $R_2$ are independently of each other selected from alkyl and alkoxy groups; $R_b$ is selected from H and alkyl groups; $R_f$ is an alkyl; and $R_3$ is selected from heterocyclic group, a phenyl group which is mono-, di-, or tri-substituted with alkoxy, alkylthio, and halo-substituted alkoxy, and

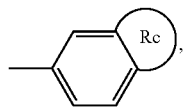

wherein Rc is selected from any bivalent carbon or heterocyclic group.

11. The compound according to claim 10, wherein $R_3$ is selected from:

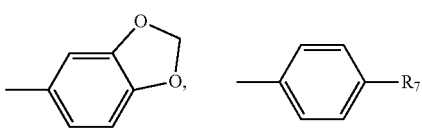

(wherein $R_7$ is —OCH$_3$, —OCH$_2$CH$_3$, —SCH$_3$, and —OCF$_3$),

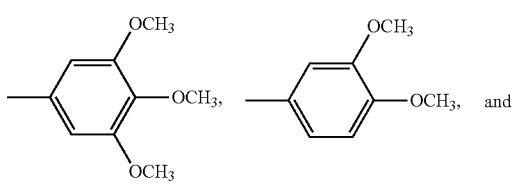

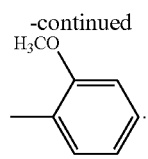

12. The compound according to claim 10, wherein $R_3$ is heterocyclic group.

13. The compound according to claim 12, wherein $R_3$ is selected from

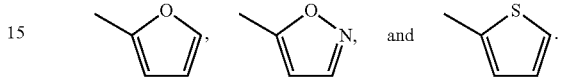

14. A pharmaceutical composition comprising an effective amount of a compound according to claim 1, or a pharmaceutically acceptable salt thereof, and a pharmaceutically acceptable carrier.

15. A method of preparing a medicament for the treatment of a cancer, comprising a step of including a compound according to claim 1 or a pharmaceutically acceptable salt thereof into the medicament.

16. The method according to claim 15, wherein the cancer is selected from cancers that are vulnerable to the interference of the calcium signal transduction in the cancer cells.

17. The method according to claim 15, wherein the cancer is selected from breast cancer, colon cancer, CNS cancer, leukemia, melanoma, non-small cell lung cancer, ovarian cancer, renal cancer, and prostate cancer.

18. The method according to claim 17, wherein the compound according to claim 1 is selected from:

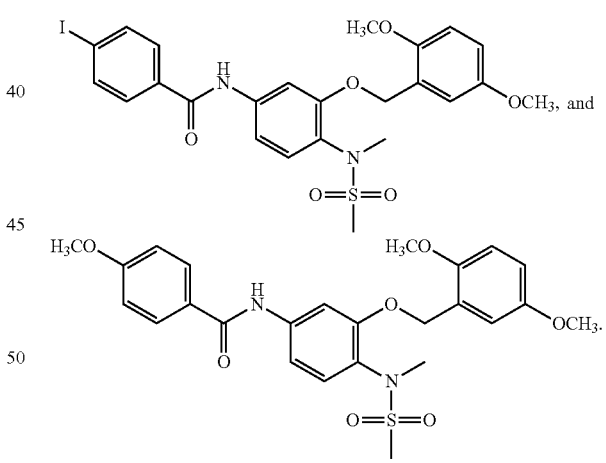

19. The method according to claim 15, wherein the cancer is breast cancer.

20. A method of preparing a medicament for the treatment of a cancer, comprising a step of including a compound according to claim 4 or a pharmaceutically acceptable salt thereof into the medicament.

21. The method according to claim 20, wherein the cancer is selected from breast cancer, colon cancer, CNS cancer, leukemia, melanoma, non-small cell lung cancer, ovarian cancer, renal cancer, and prostate cancer.

22. The method according to claim 21, wherein the compound according to claim 4 is:

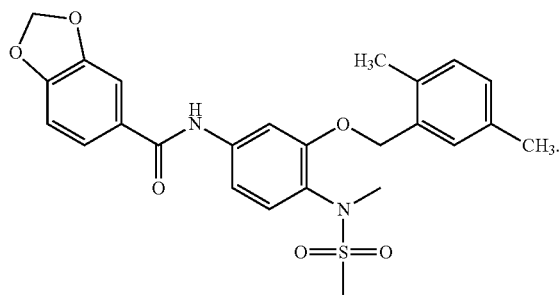 [SMILES: Cc1ccc(C)c(COc2cc(NC(=O)c3ccc4c(c3)OCO4)ccc2N(C)S(C)(=O)=O)c1]

23. A method of treating a cancer, comprising administering to a mammal a therapeutically effective amount of a compound according to claim 1, or a pharmaceutically acceptable salt thereof.

24. The method according to claim 23, wherein the cancer is selected from cancers that are vulnerable to the interference of the calcium signal transduction in the cancer cells.

25. The method according to claim 23, wherein the cancer is selected from breast cancer, colon cancer, CNS cancer, leukemia, melanoma, non-small cell lung cancer, ovarian cancer, renal cancer, and prostate cancer.

26. The method according to claim 25, wherein the compound according to claim 1 is selected from:

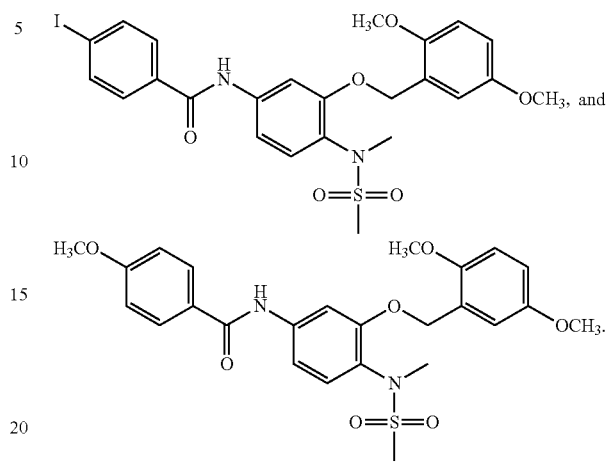

27. The method according to claim 23, wherein the cancer is breast cancer.

* * * * *